(12) United States Patent
Henke et al.

(10) Patent No.: US 12,048,570 B2
(45) Date of Patent: Jul. 30, 2024

(54) UNLOCKING APPARATUS AND STRAINER BASKET

(71) Applicant: Aesculap AG, Tuttlingen (DE)

(72) Inventors: Matthias Henke, Villingen-Schwenningen (DE); Daniel Kiessling, Villingen-Schwenningen (DE); Sebastian Luz, Emmingen-Liptingen (DE)

(73) Assignee: Aesculap AG, Tuttlingen (DE)

( * ) Notice: Subject to any disclaimer, the term of this patent is extended or adjusted under 35 U.S.C. 154(b) by 107 days.

(21) Appl. No.: 17/902,960

(22) Filed: Sep. 5, 2022

(65) Prior Publication Data

US 2023/0134498 A1     May 4, 2023

Related U.S. Application Data

(63) Continuation of application No. PCT/EP2021/055247, filed on Mar. 3, 2021.

(30) Foreign Application Priority Data

Mar. 6, 2020     (DE) ...................... 10 2020 106 102.1

(51) Int. Cl.
  *A61B 50/20*     (2016.01)
  *A61B 50/34*     (2016.01)
  (Continued)

(52) U.S. Cl.
  CPC .............. *A61B 50/34* (2016.02); *A61B 50/20* (2016.02); *A61L 2/07* (2013.01); *A61L 2/26* (2013.01);
  (Continued)

(58) Field of Classification Search
  CPC ......... A61B 50/20; A61B 50/34; A61B 90/70; A61B 50/22; A61L 2/07; A61L 2/26; A61L 2202/17; A61L 2202/24
  (Continued)

(56) References Cited

U.S. PATENT DOCUMENTS 2,559,636 A * 7/1951 King ...................... A45C 11/00
                                                                206/370
2,906,410 A * 9/1959 McGuire ................ A61B 50/20
                                                                D24/228
(Continued)

FOREIGN PATENT DOCUMENTS

DE     102017102027 A1     8/2018
DE     102020106102 A1 *   9/2021 ............. A61B 50/20
(Continued)

OTHER PUBLICATIONS

Search Report received in International Application No. PCT/EP2021/055247 dated Jun. 7, 2021, with translation, 5 pages.
(Continued)

*Primary Examiner* — Jennifer E. Novosad
(74) *Attorney, Agent, or Firm* — Christopher A. Rothe; Culhane PLLC

(57) ABSTRACT

An unlocking apparatus for unlocking locking devices of at least two medical ring instruments, and a sieve basket. The locking devices include cooperating locking elements, and the unlocking apparatus includes a first receiving body with at least two ring receptacles for accommodating first rings of the at least two ring instruments. The unlocking apparatus includes an unlocking body with at least two unlocking elements cooperating with second rings of the at least two ring instruments. The unlocking body and the receiving body are movable relative to one another in an actuating direction such that the at least two unlocking elements engage on and move the second rings relative to the first
(Continued)

Figure 1:
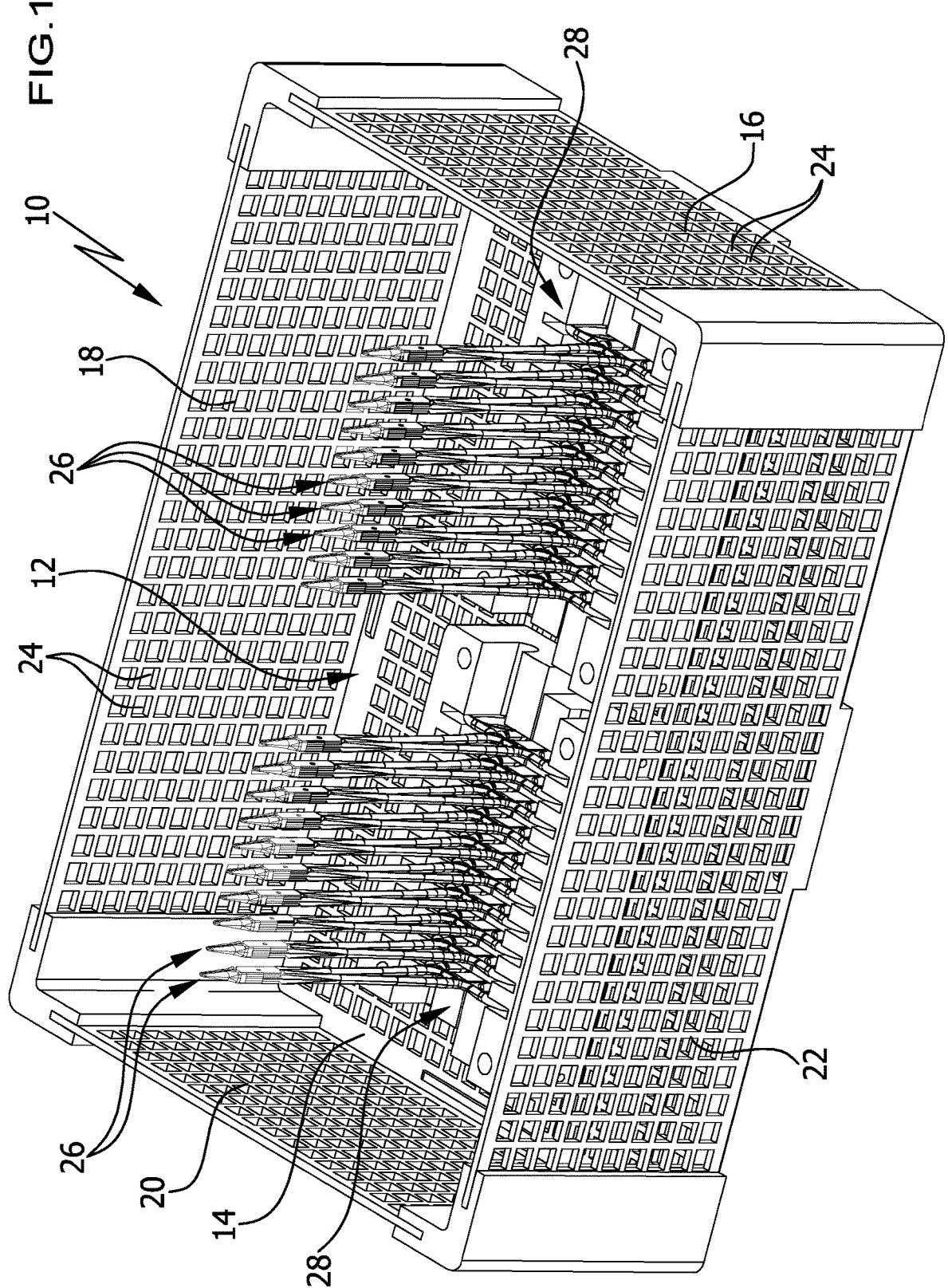

rings in an unlocking direction that is transverse, in particular perpendicular, to a first ring plane and to a second ring plane for transferring the locking devices from a locked position into an unlocked position.

20 Claims, 24 Drawing Sheets

(51) Int. Cl.
  *A61L 2/07* (2006.01)
  *A61L 2/26* (2006.01)
  *A61B 90/70* (2016.01)
(52) U.S. Cl.
  CPC ........... *A61B 90/70* (2016.02); *A61L 2202/17* (2013.01); *A61L 2202/24* (2013.01)
(58) Field of Classification Search
  USPC ........ 211/85.13, 4, 70.6; 206/363, 368, 369, 206/375; 422/300, 301
  See application file for complete search history.

(56) References Cited

U.S. PATENT DOCUMENTS

| | | | | |
|---|---|---|---|---|
| 3,564,662 A * | 2/1971 | Dold | ..................... | A61B 50/10 206/370 |
| 3,925,014 A * | 12/1975 | Langdon | ................... | A61L 2/26 206/370 |
| 4,229,420 A * | 10/1980 | Smith | ..................... | A61B 50/22 606/1 |
| 4,342,391 A * | 8/1982 | Schainholz | ............ | A61B 50/20 206/370 |
| 4,577,755 A * | 3/1986 | Ramsay | ..................... | A61L 2/26 206/370 |
| 4,641,749 A * | 2/1987 | Link | ....................... | A61B 50/20 206/370 |
| 4,643,303 A * | 2/1987 | Arp | ........................... | A61L 2/26 206/370 |
| 4,865,821 A * | 9/1989 | Langdon | ................. | A61B 50/22 422/561 |
| 5,137,151 A * | 8/1992 | Choate | ................... | A61B 50/20 206/370 |
| 5,215,726 A * | 6/1993 | Kudla | ...................... | A61L 2/26 206/370 |
| 5,449,069 A * | 9/1995 | Pijanowski | ............ | A61B 50/20 206/370 |
| 5,451,380 A * | 9/1995 | Zinnanti | ................ | A61B 50/20 206/370 |
| 6,230,888 B1 * | 5/2001 | Frieze | .................... | A61B 50/22 206/370 |
| 6,534,000 B1 * | 3/2003 | Michaelson | .............. | A61L 2/26 422/26 |
| 7,461,751 B2 * | 12/2008 | Lyons | .................... | A61B 50/13 211/85.13 |
| 7,871,581 B1 * | 1/2011 | Coleman | ................ | A61B 50/20 211/85.13 |
| 8,641,984 B2 * | 2/2014 | Alston | ................... | A61B 50/30 206/370 |
| 9,156,571 B2 * | 10/2015 | Ramkhelawan | ....... | A61B 50/22 |
| 9,198,811 B2 * | 12/2015 | Pizzato | ................... | A61F 17/00 |
| 9,339,338 B2 * | 5/2016 | Ramkhelawan | ....... | A61B 50/34 |
| 10,456,494 B2 * | 10/2019 | Roudebush | ............... | A61L 2/26 |
| 11,191,603 B1 * | 12/2021 | Schor | ..................... | A47B 81/00 |
| 2004/0206711 A1 * | 10/2004 | Hoftman | ................ | A61B 50/20 211/85.13 |
| 2007/0104609 A1 * | 5/2007 | Powell | ..................... | A61L 2/26 206/370 |
| 2009/0152414 A1 * | 6/2009 | Lyons | .................... | A61B 50/24 248/176.1 |
| 2011/0114522 A1 | 5/2011 | Alston et al. | | |
| 2012/0234781 A1 * | 9/2012 | Cogliano | ................. | B25H 3/06 211/85.13 |
| 2013/0074450 A1 * | 3/2013 | Higham | ................. | A61B 50/30 206/370 |
| 2013/0108503 A1 * | 5/2013 | Ramkhelawan | ....... | A61B 50/34 422/1 |
| 2014/0216966 A1 * | 8/2014 | Ramkhelawan | ....... | A61B 50/30 206/370 |
| 2015/0374439 A1 * | 12/2015 | Ramkhelawan | ....... | A61B 50/34 211/85.13 |
| 2019/0343540 A1 | 11/2019 | Morales et al. | | |
| 2023/0134498 A1 * | 5/2023 | Henke | ................... | A61B 50/22 206/370 |

FOREIGN PATENT DOCUMENTS

| | | | | |
|---|---|---|---|---|
| DE | 102020129618 A1 * | 5/2022 | | |
| EP | 3923850 B1 * | 4/2023 | ............ | A61B 50/20 |
| WO | WO-9936106 A1 * | 7/1999 | ............ | A61B 50/20 |
| WO | 2013062925 A1 | 5/2013 | | |
| WO | WO-2021175883 A1 * | 9/2021 | ............ | A61B 50/20 |

OTHER PUBLICATIONS

Written Opinion received in International Application No. PCT/EP2021/055247 dated Jun. 7, 2021, with translation, 10 pages.

* cited by examiner

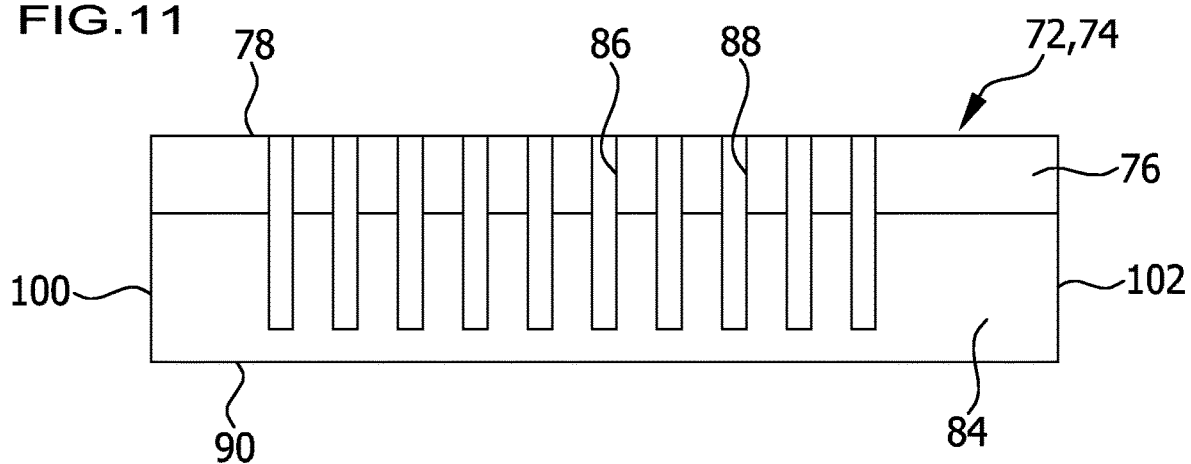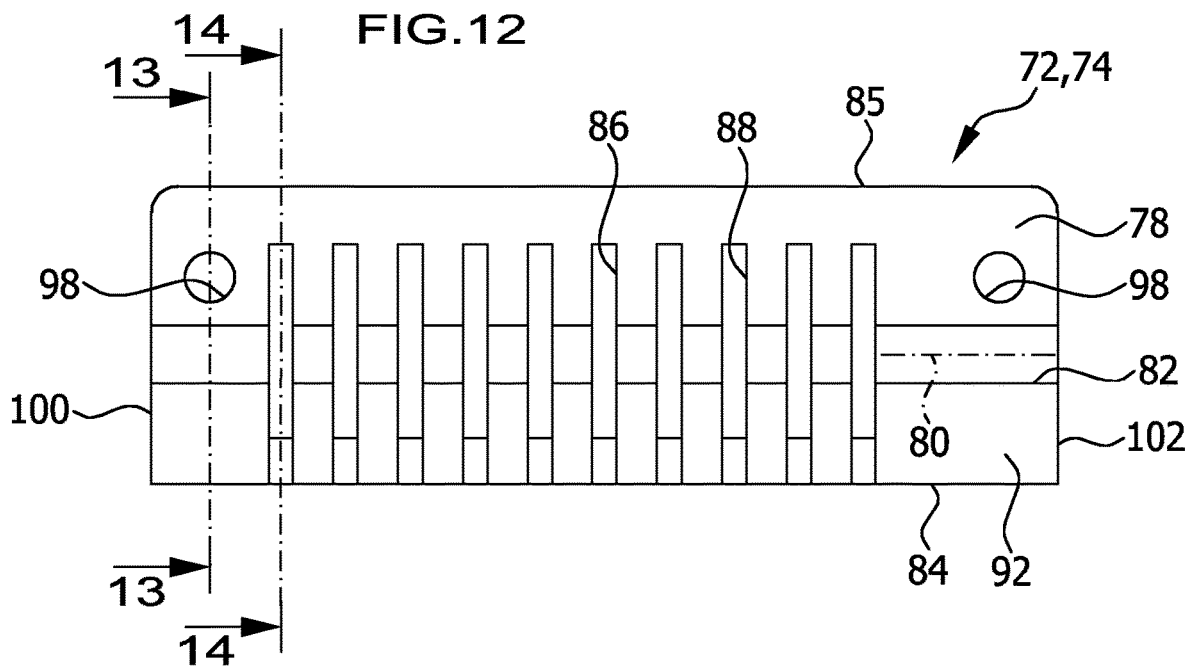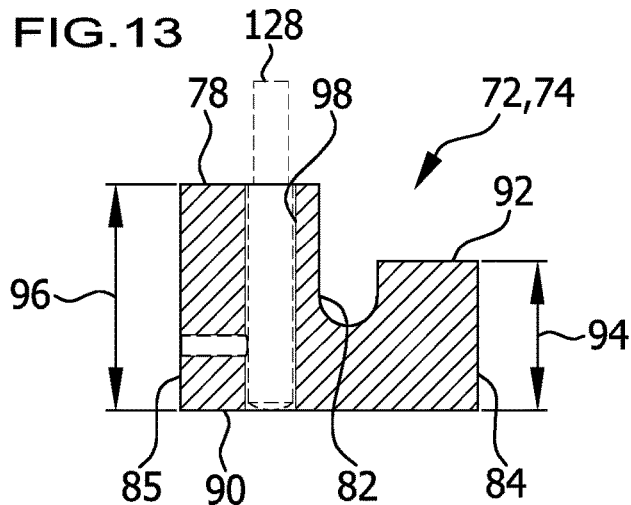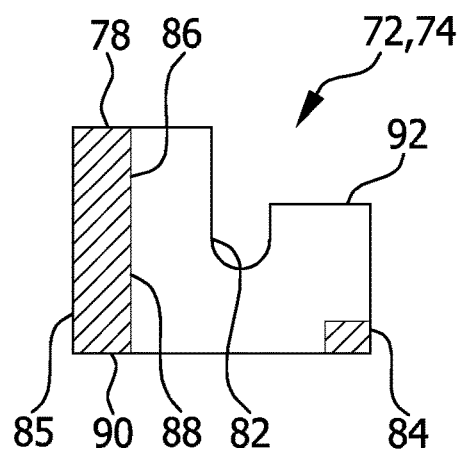

UNLOCKING APPARATUS AND STRAINER BASKET

CROSS-REFERENCE TO RELATED APPLICATIONS

This application is a continuation of international application number PCT/EP2021/055247 filed on Mar. 3, 2021 and claims the benefit of German application number 10 2020 106 102.1 filed on Mar. 6, 2020.

The present disclosure relates to the subject matter disclosed in international application number PCT/EP2021/055247 of Mar. 3, 2021 and German application number 10 2020 106 102.1 of Mar. 6, 2020, which are incorporated herein by reference in their entireties and for all purposes.

FIELD

The present disclosure relates to unlocking apparatuses generally, and more specifically to an unlocking apparatus for unlocking locking devices of at least two medical ring instruments, said locking devices comprising cooperating locking elements.

Furthermore, the present disclosure relates to sieve baskets generally, and more specifically to a sieve basket with a receiving space for accommodating surgical instruments.

BACKGROUND

Typically, a plurality of instruments for surgical procedures are provided in sieve baskets, also called sieve trays or strainer baskets. The instruments must be reprocessed after a procedure, namely regardless of whether they were used during the procedure or not. Typically a proportion of ring instruments with locking devices, also simply called locks, in a sieve tray is high. The ring instruments may be, in particular, needle holders and all kinds of clamps.

In order to be able to achieve a good cleaning result, these ring instruments must be processed in their open state. Until now, this has required unlocking the locking device on each instrument by hand. The cooperating locking elements of the locking devices must thereby be brought out of engagement, which is also referred to as disengaging the locking elements. After unlocking, the instruments must still be opened.

The manual unlocking and opening of the ring instruments increases a preparation time for a reprocessing process. In addition, the repeated execution of the described unlocking operation can cause pain in the hands and fingers of a user.

SUMMARY

In a first aspect, an unlocking apparatus for unlocking locking devices of at least two medical ring instruments is provided. The locking devices comprising cooperating locking elements. The cooperating locking elements are in force-locking and/or positive-locking engagement in a locked position and are out of engagement in an unlocked position. The ring instruments each comprise a first branch with a first distal end and a first proximal end and each comprise a second branch with a second distal end and a second proximal end. The first branch and the second branch of each ring instrument are mounted on one another so as to be pivotable about a pivot axis. A first ring is arranged or formed on the first proximal end of the first branch of each ring instrument and a second ring is arranged or formed on the second proximal end of the second branch of each ring instrument. Each first ring defines a first ring plane and each second ring defines a second ring plane. The first ring plane and the second ring plane of each ring instrument run in parallel or substantially in parallel to one another. The pivot axis runs transversely, in particular perpendicularly, to the first ring plane and/or to the second ring plane. The unlocking apparatus comprises a receiving body with at least two ring receptacles for accommodating the first rings of the at least two ring instruments. The unlocking apparatus comprises an unlocking body with at least two unlocking elements cooperating with the second rings of the at least two ring instruments. The unlocking body and the receiving body are arranged so as to be movable relative to one another in an actuating direction in such a way that the at least two unlocking elements thereby engage on the second rings and move same relative to the first rings in an unlocking direction transversely, in particular perpendicularly, to the first ring plane and to the second ring plane for transferring the locking devices of the at least two ring instruments from the locked position into the unlocked position.

In a second aspect, a sieve basket with a receiving space for accommodating surgical instrument is provided. An unlocking apparatus for unlocking locking devices of at least two medical ring instruments is arranged in the receiving space. The locking devices comprising cooperating locking elements. The cooperating locking elements are in force-locking and/or positive-locking engagement in a locked position and are out of engagement in an unlocked position. The ring instruments each comprise a first branch with a first distal end and a first proximal end and each comprise a second branch with a second distal end and a second proximal end. The first branch and the second branch of each ring instrument are mounted on one another so as to be pivotable about a pivot axis. A first ring is arranged or formed on the first proximal end of the first branch of each ring instrument and a second ring is arranged or formed on the second proximal end of the second branch of each ring instrument. Each first ring defines a first ring plane, and each second ring defines a second ring plane. The first ring plane and the second ring plane of each ring instrument run in parallel or substantially in parallel to one another. The pivot axis runs transversely, in particular perpendicularly, to the first ring plane and/or to the second ring plane. The unlocking apparatus comprises a receiving body with at least two ring receptacles for accommodating the first rings of the at least two ring instruments. The unlocking apparatus comprises an unlocking body with at least two unlocking elements cooperating with the second rings of the at least two ring instruments. The unlocking body and the receiving body are arranged so as to be movable relative to one another in an actuating direction in such a way that the at least two unlocking elements thereby engage on the second rings and move same relative to the first rings in an unlocking direction transversely, in particular perpendicularly, to the first ring plane and to the second ring plane for transferring the locking devices of the at least two ring instruments from the locked position into the unlocked position.

BRIEF DESCRIPTION OF THE DRAWING FIGURES

Figure 2:
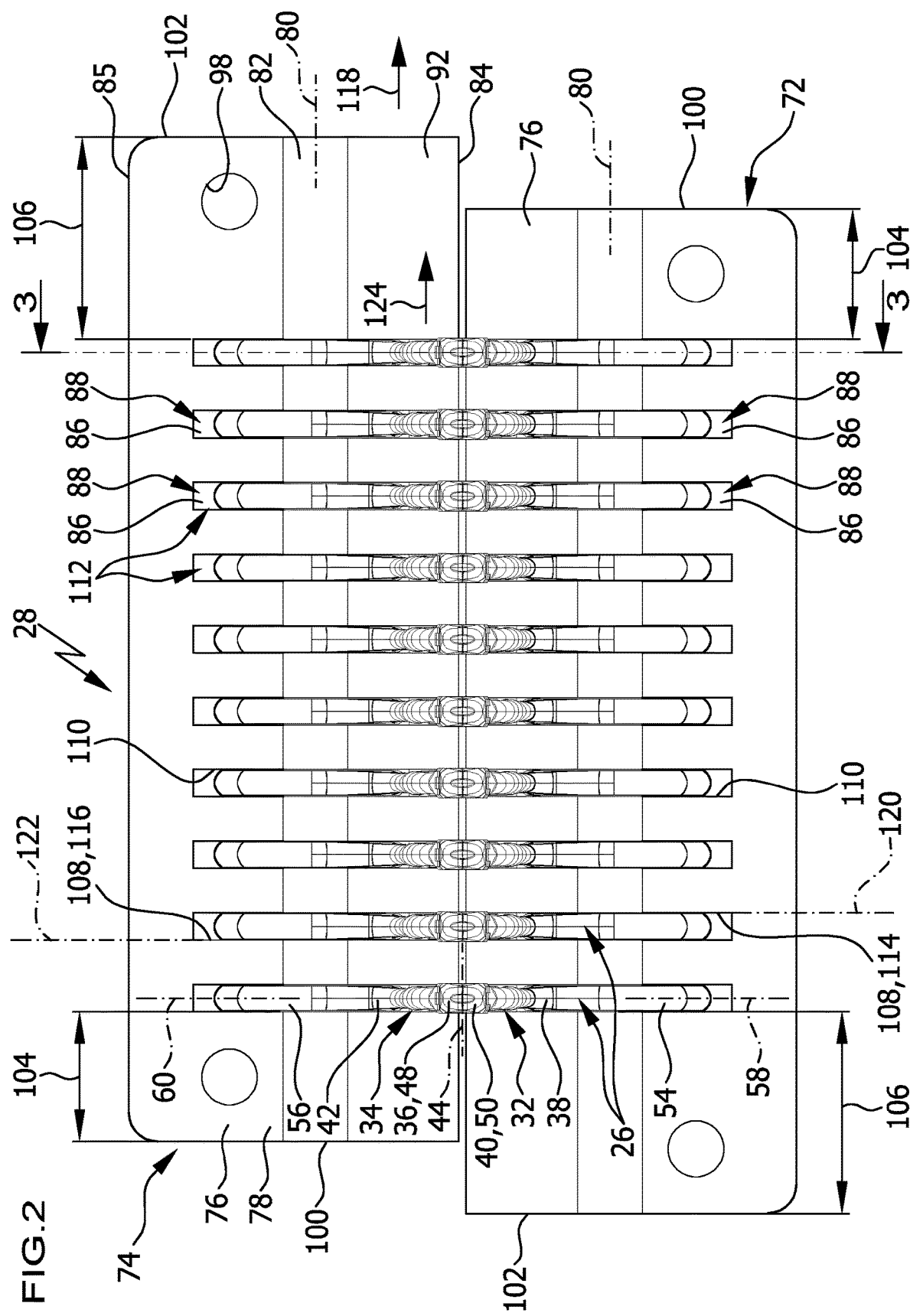
Figure 3:
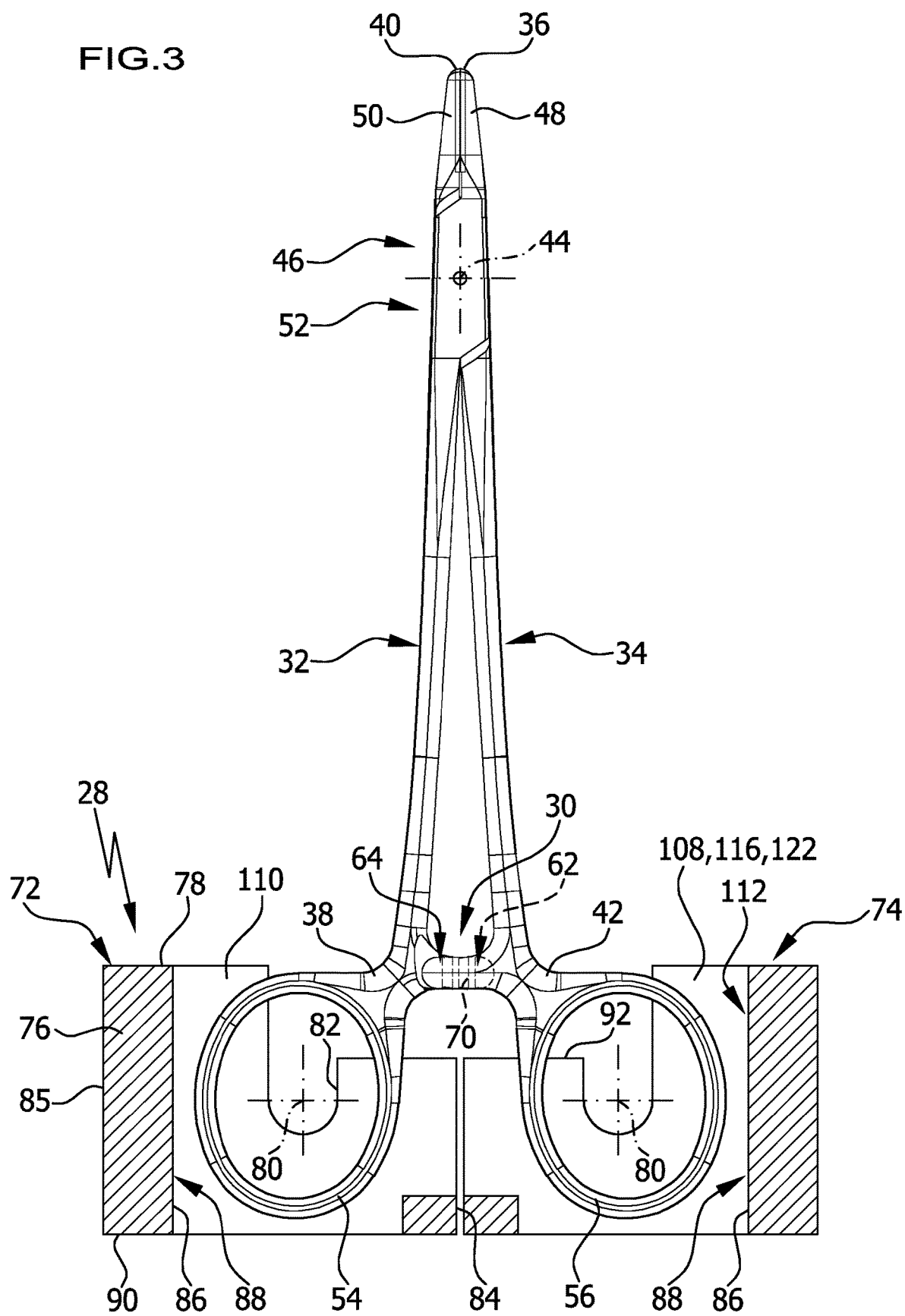
Figure 4:
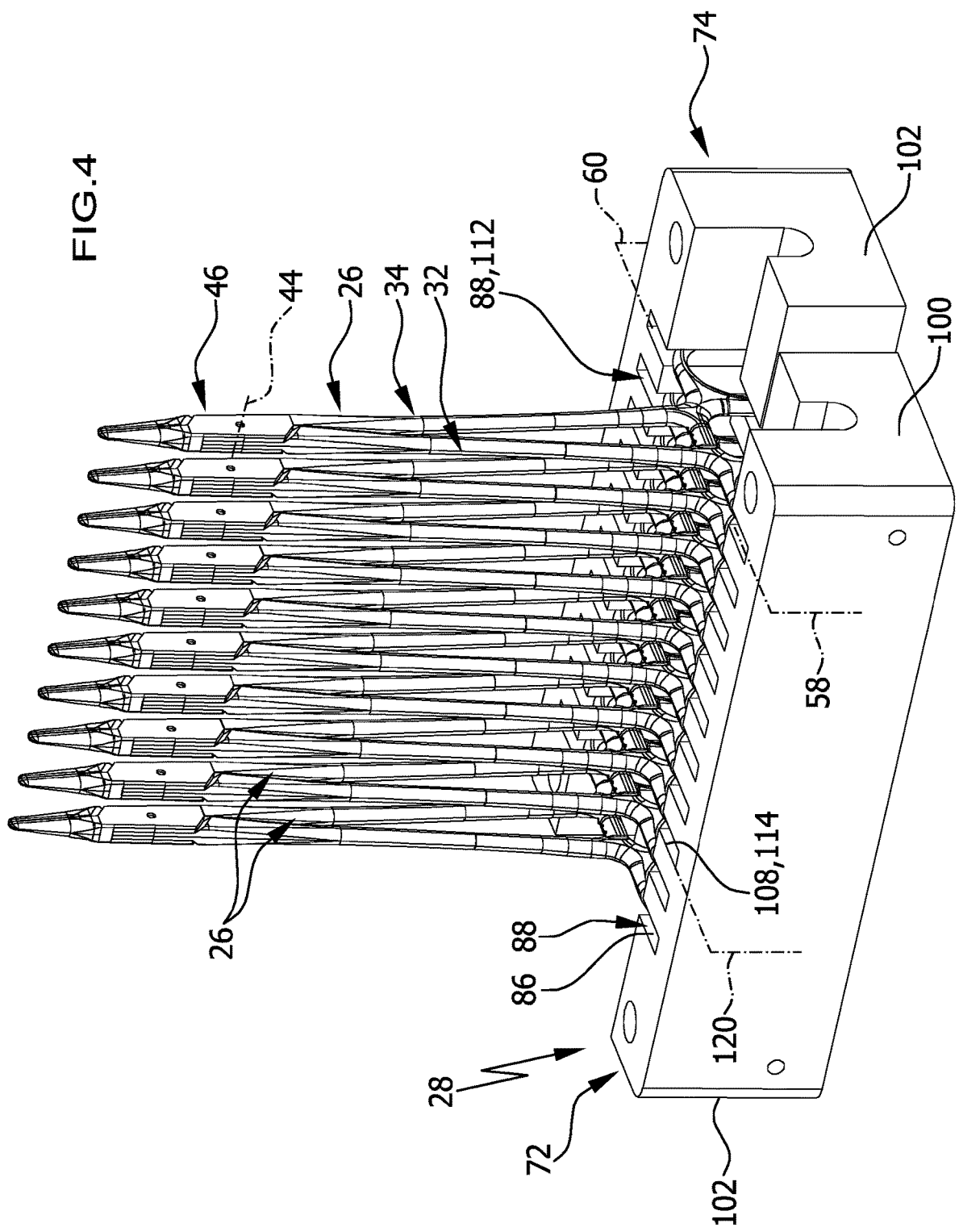
Figure 5:
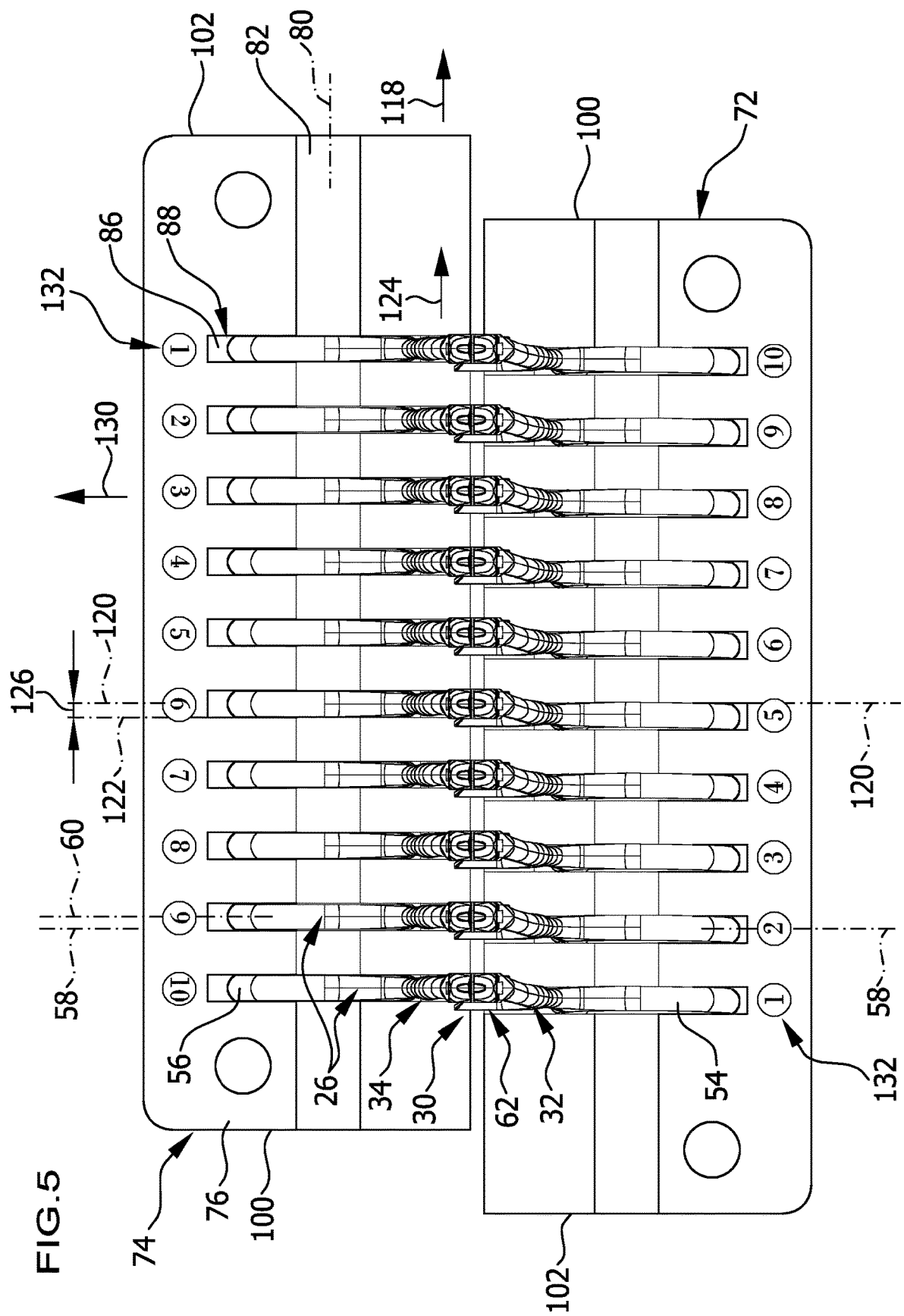
Figure 6:
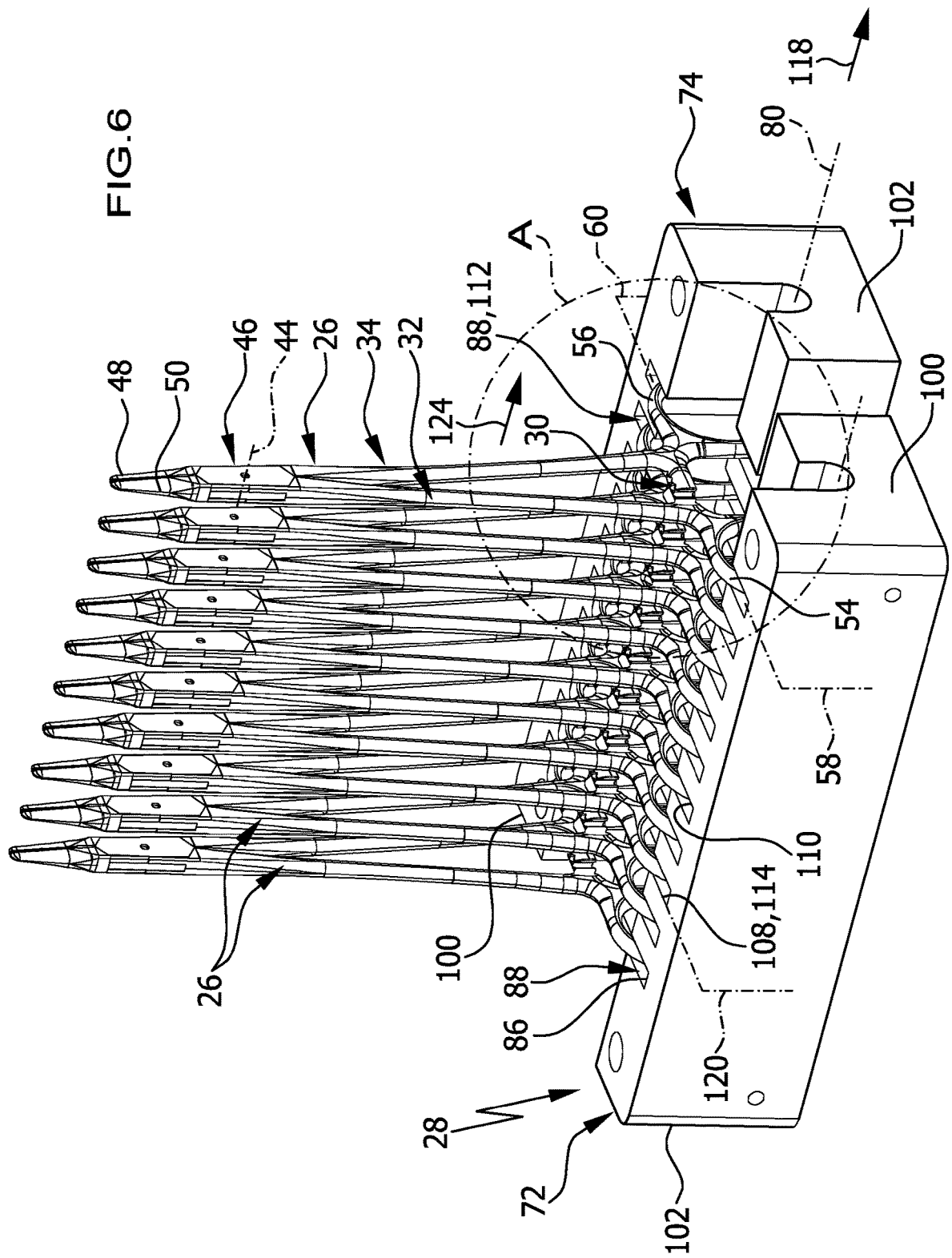
Figure 7:
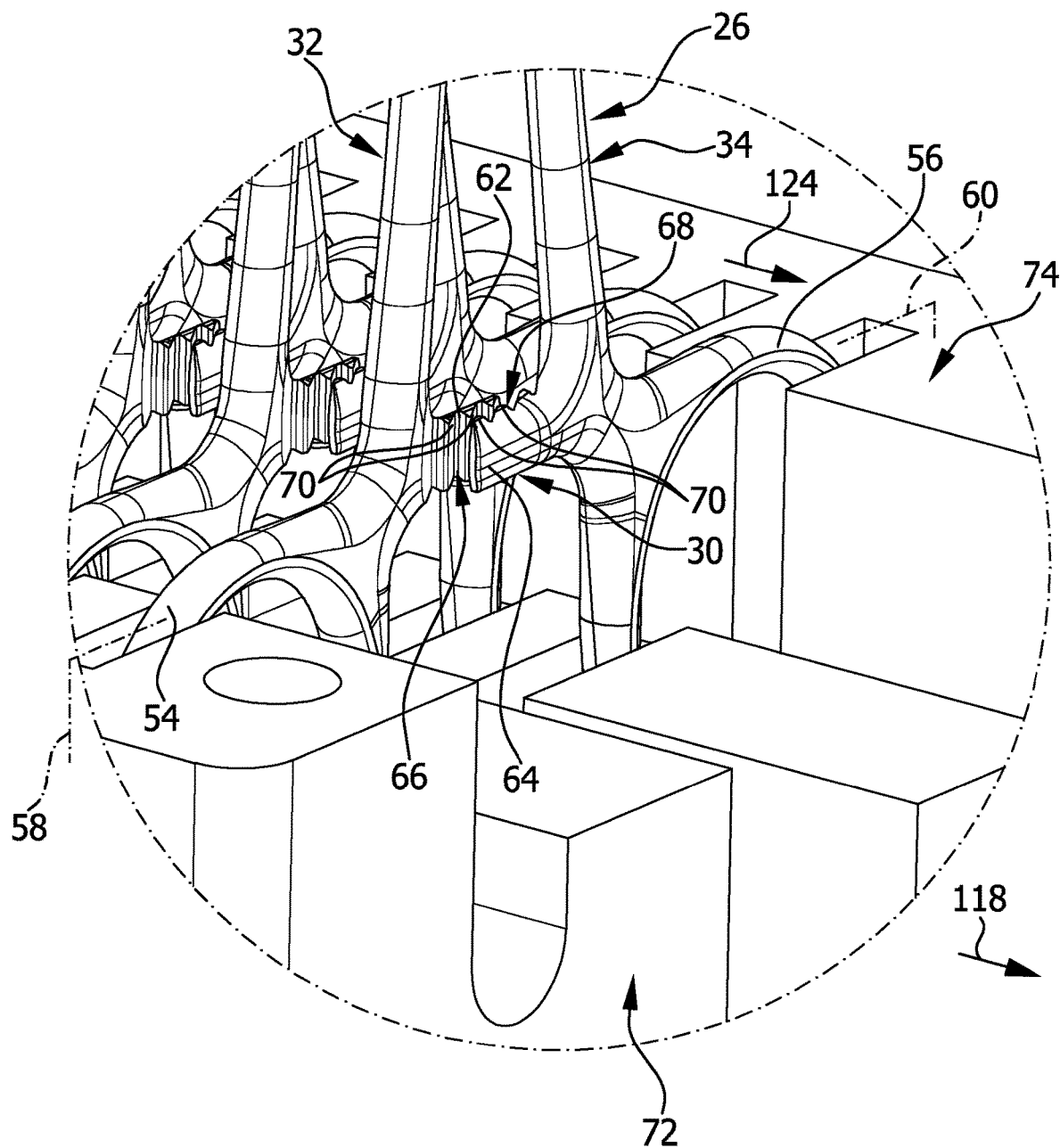
Figure 8:
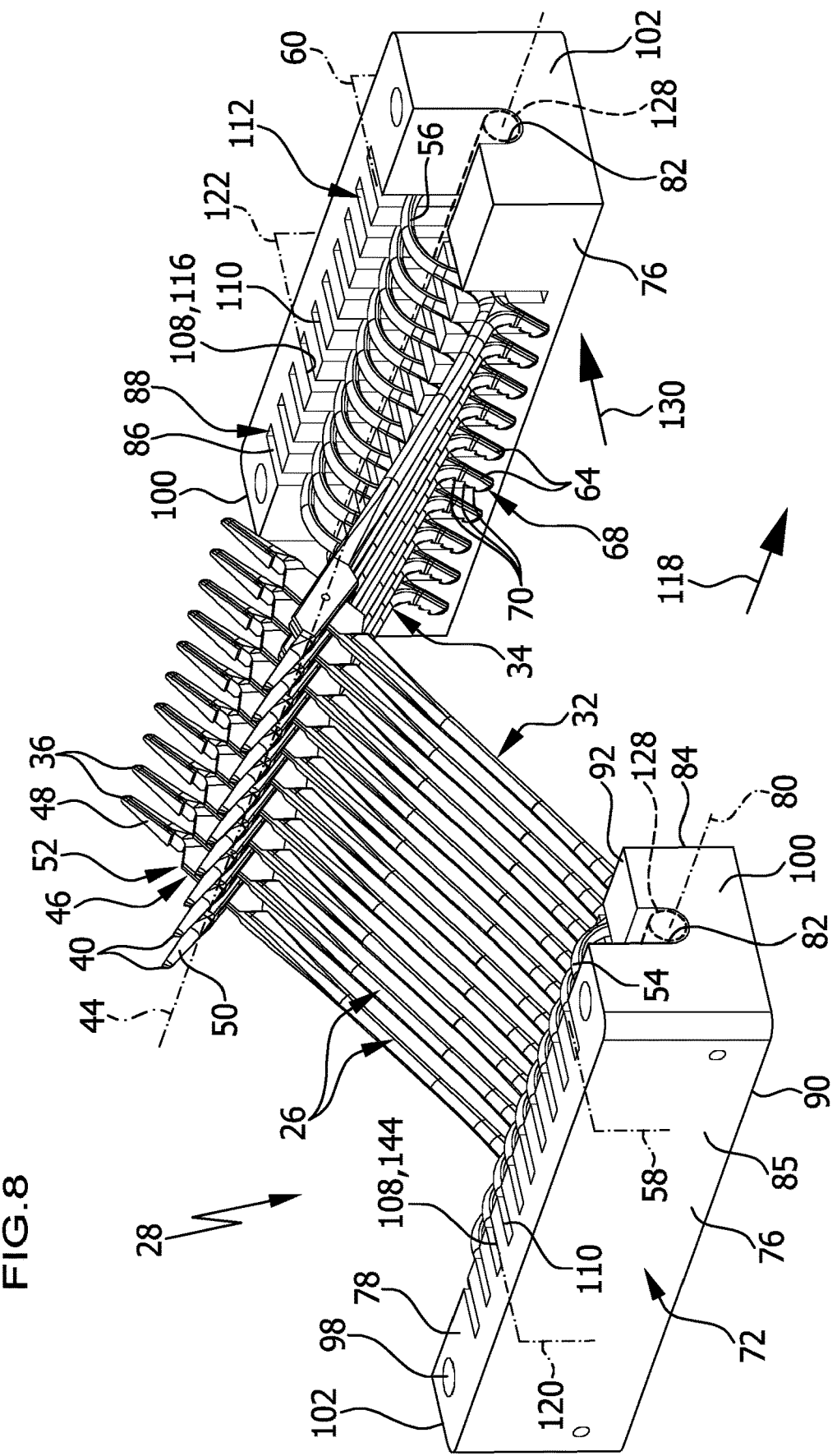
Figure 9:
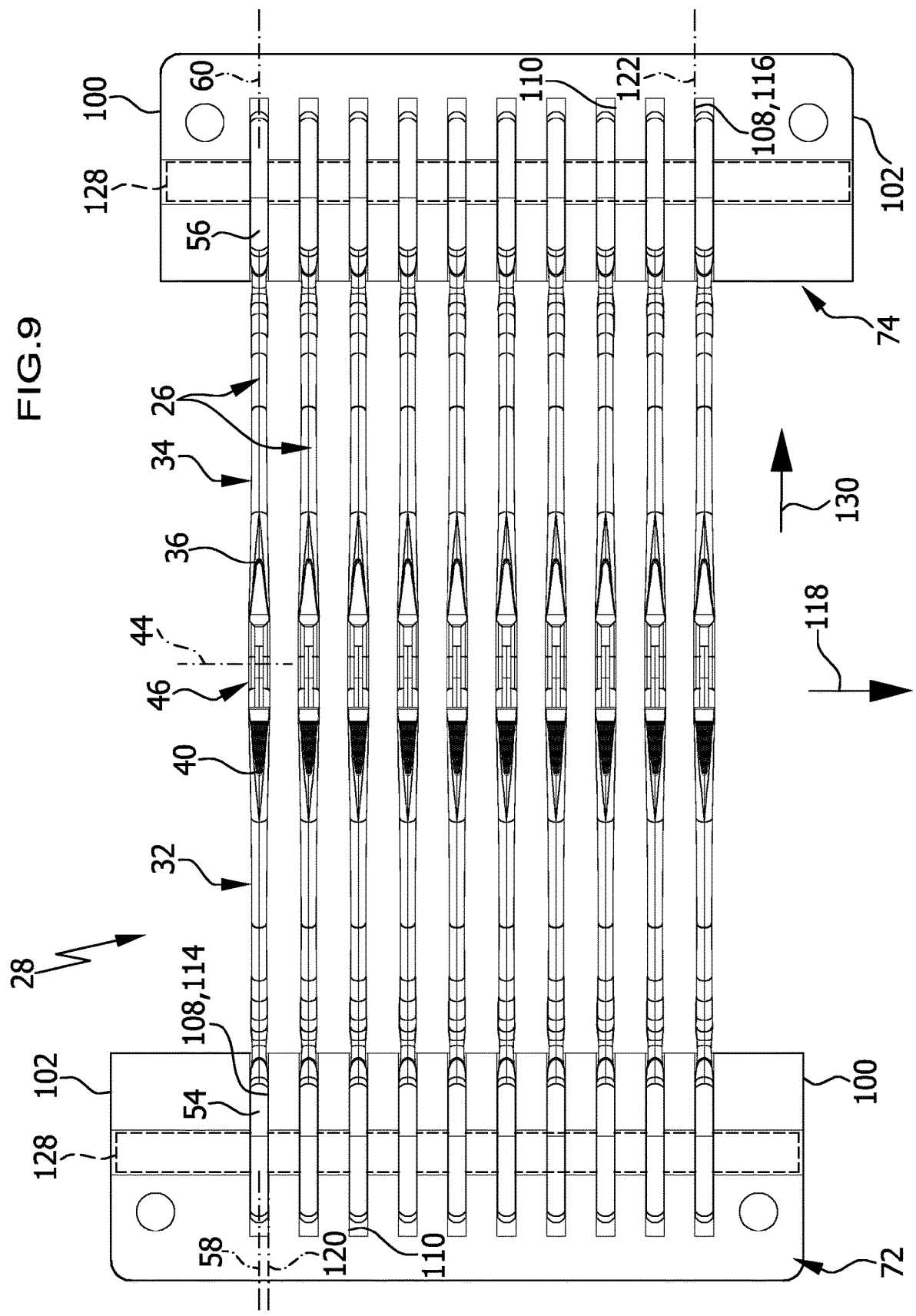
Figure 10:
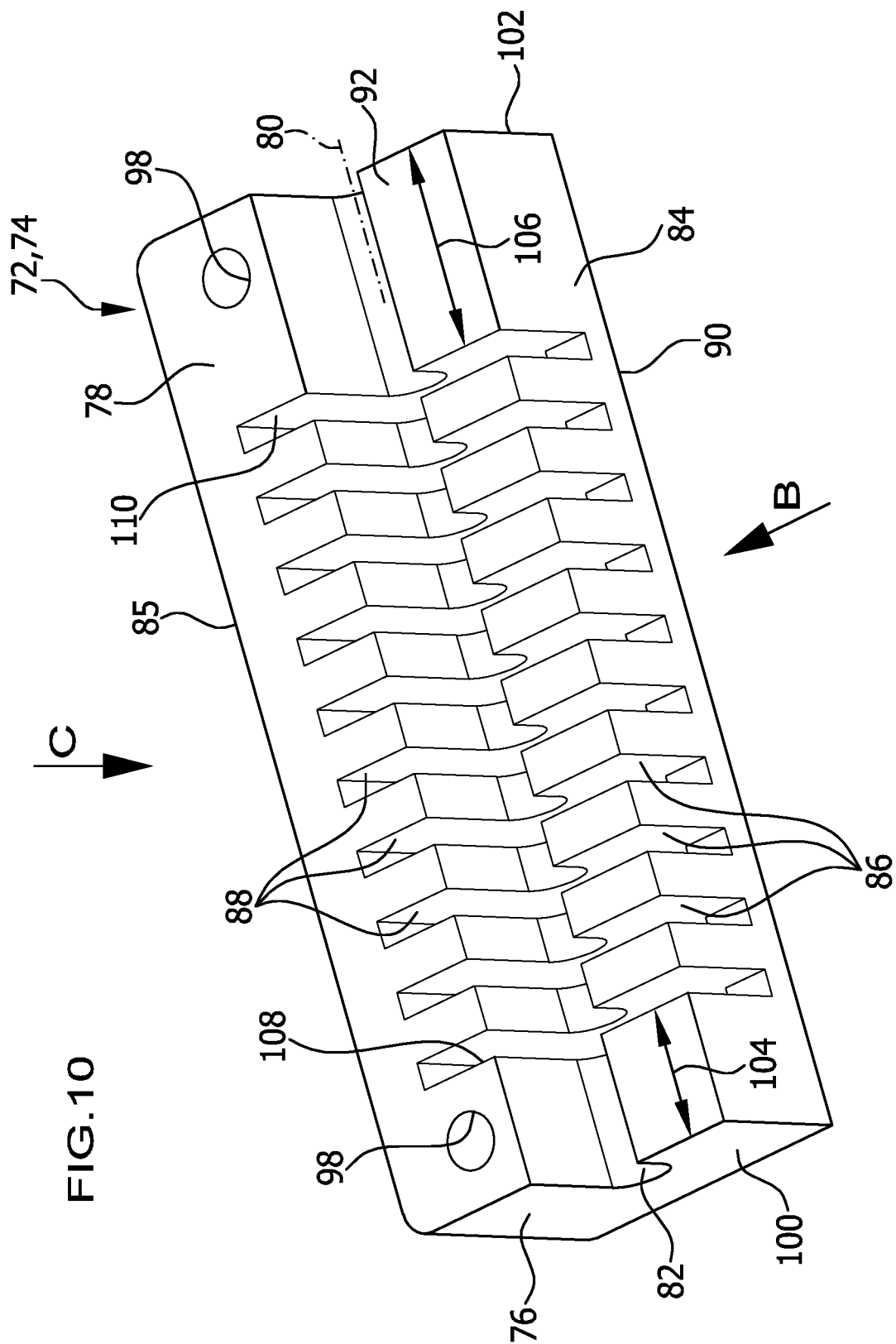
Figure 15:
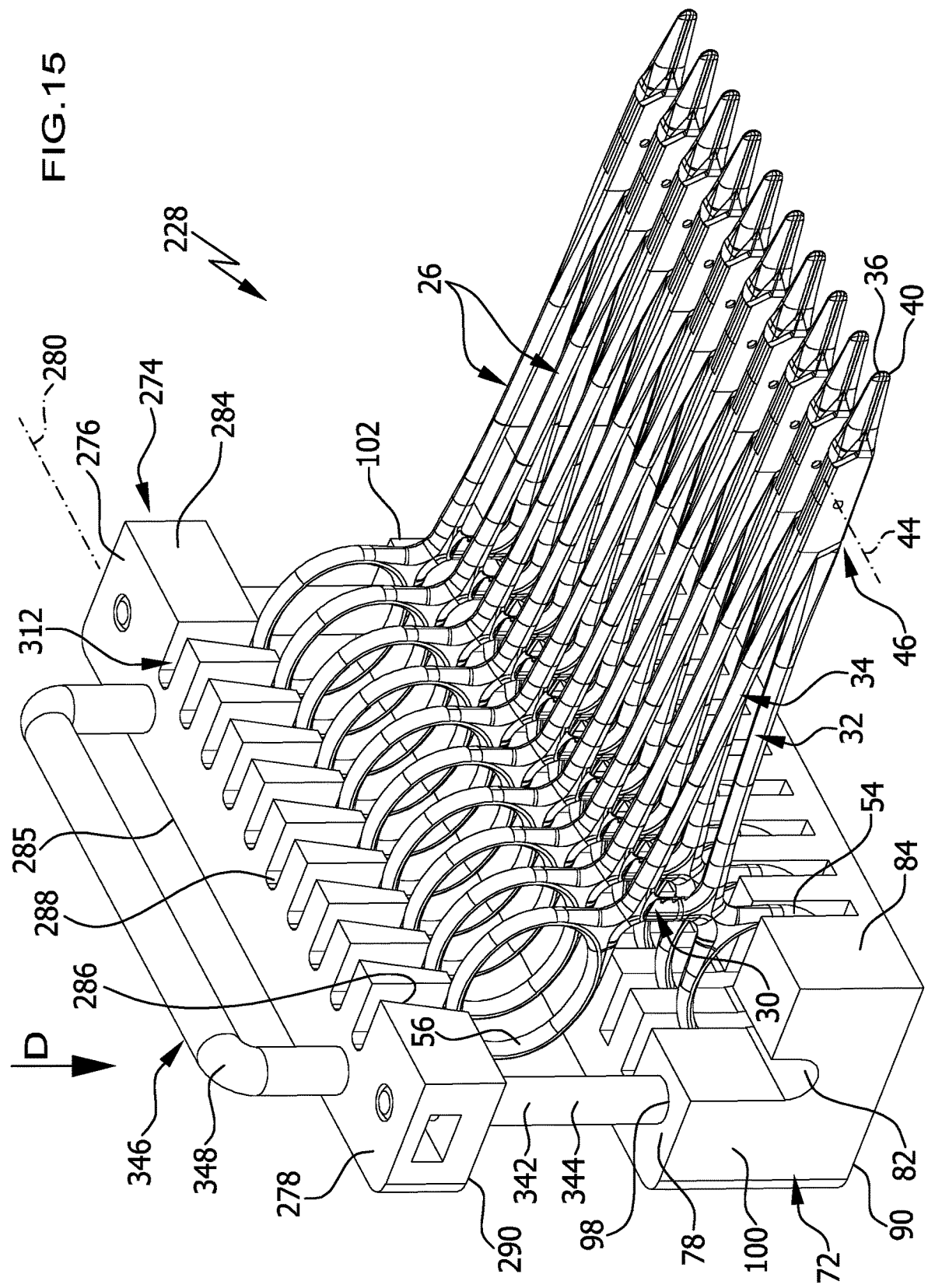
Figure 16:
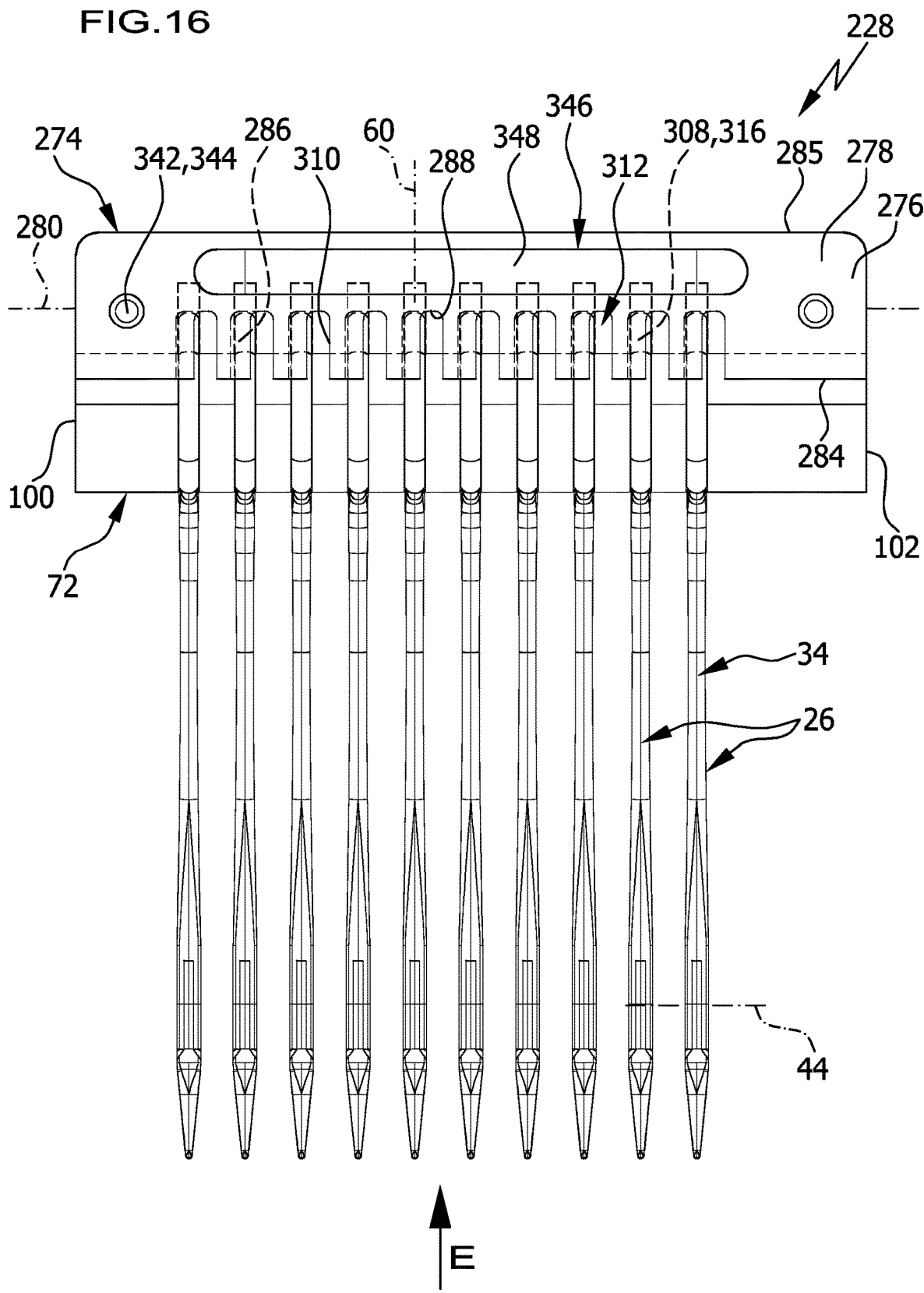
Figure 17:
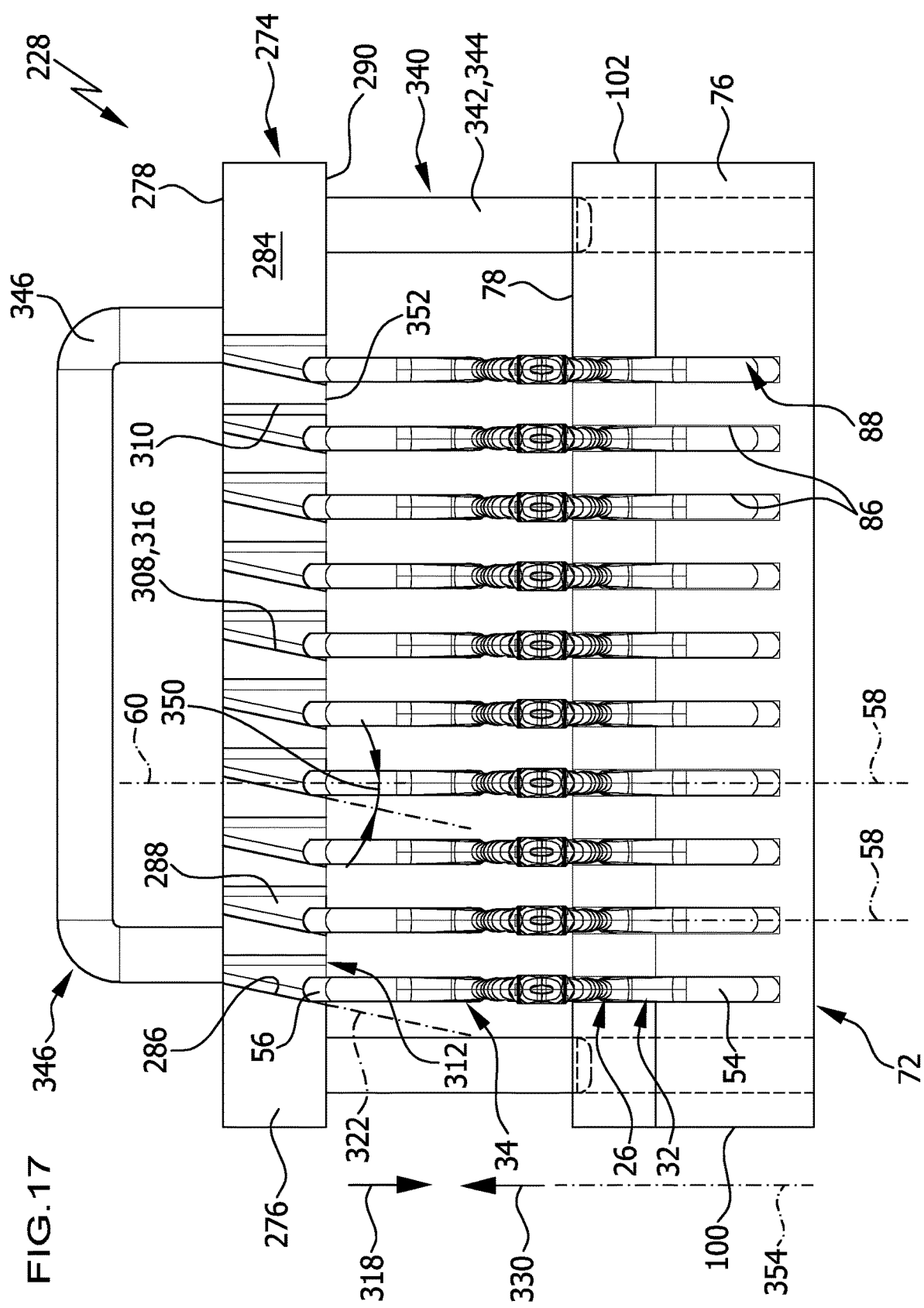
Figure 18:
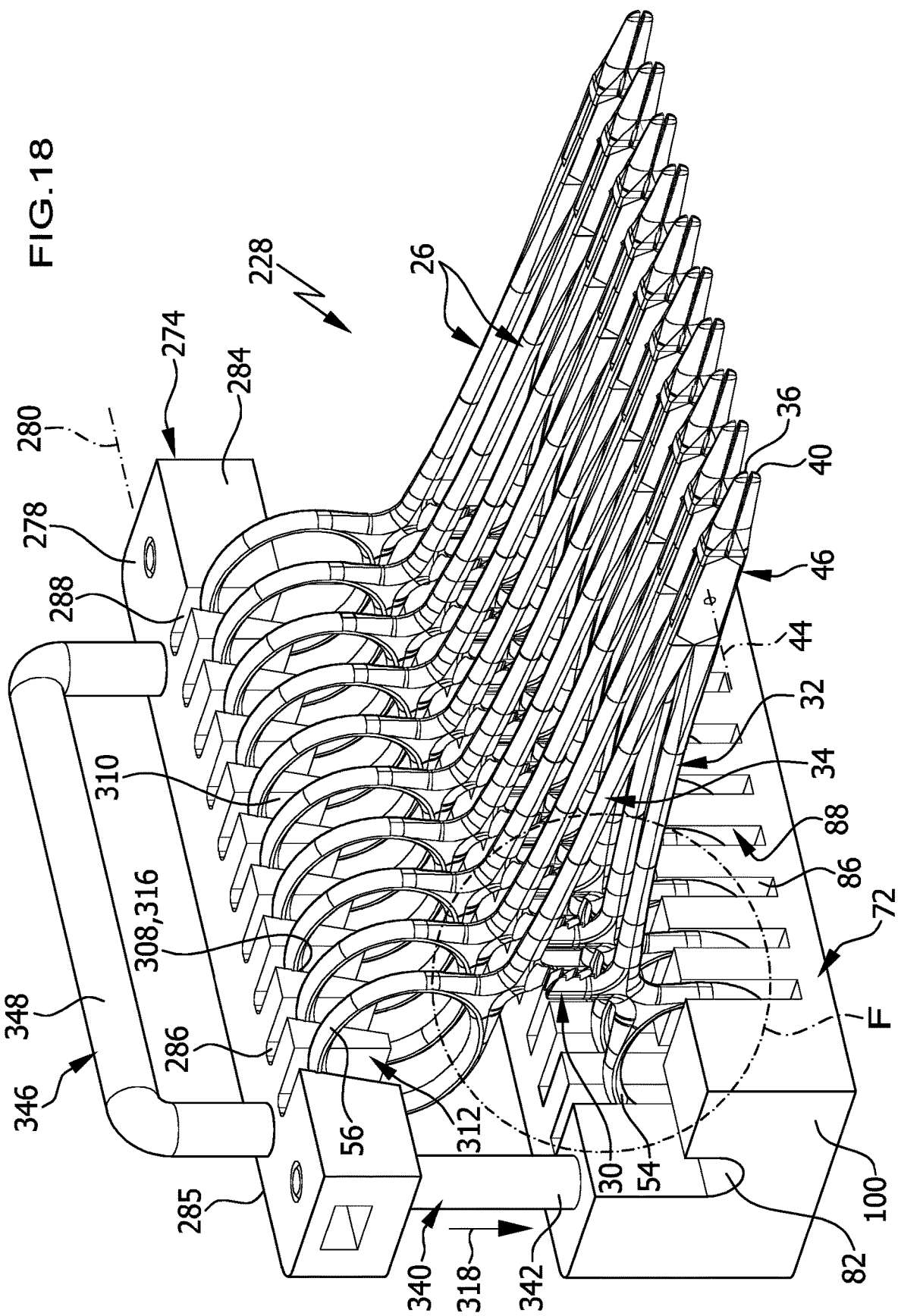
Figure 19:
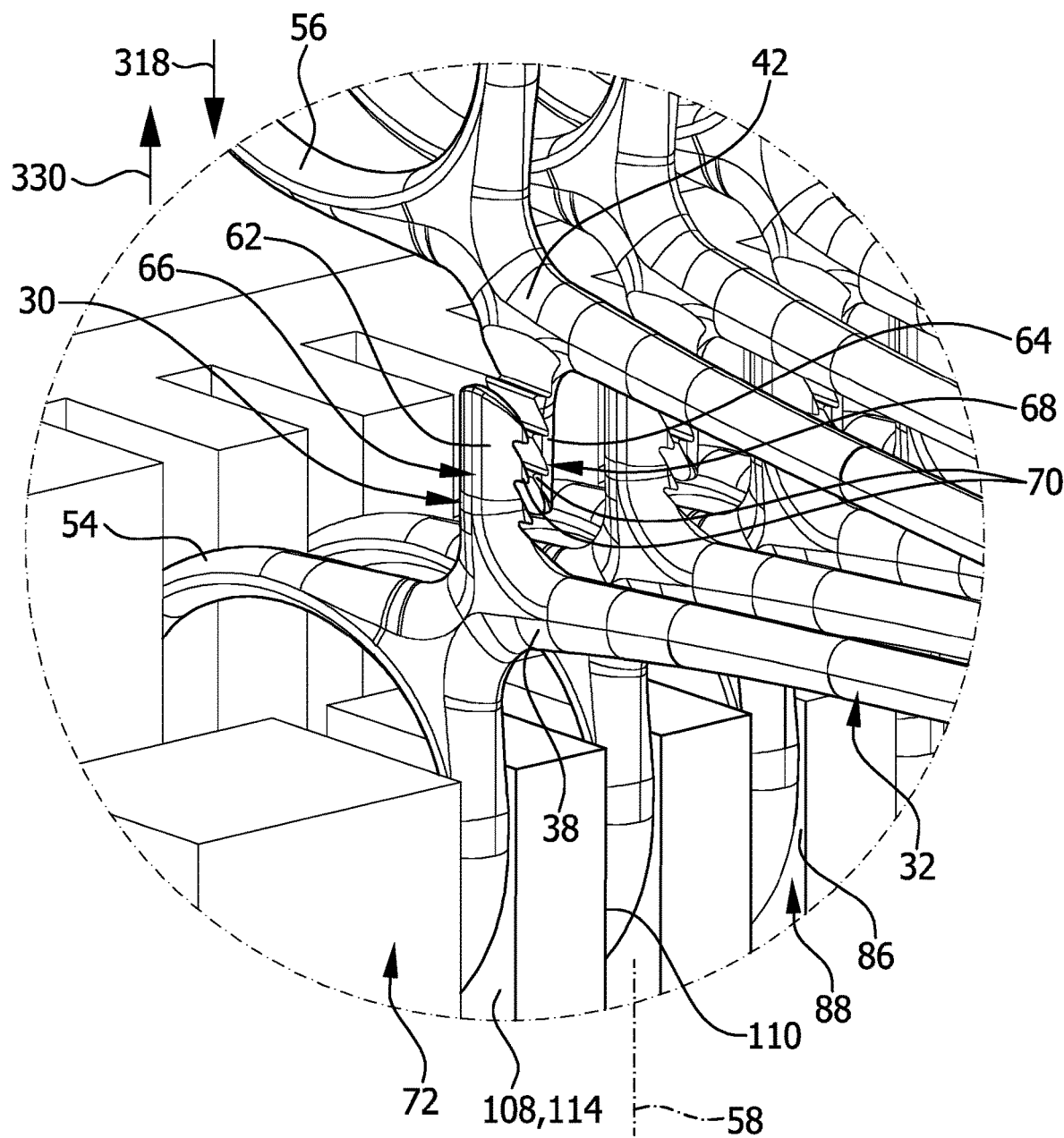
Figure 20:
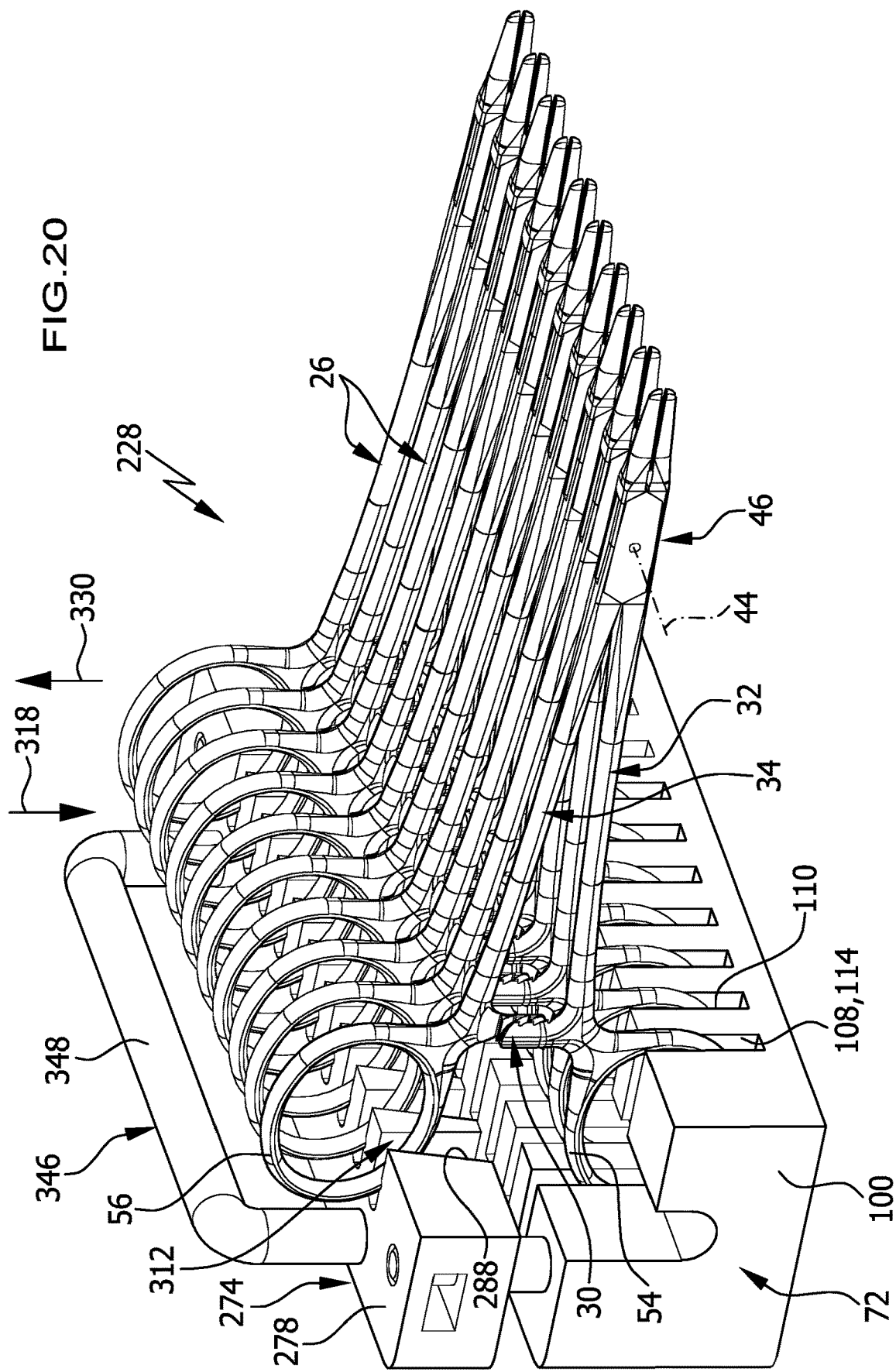
Figure 21:
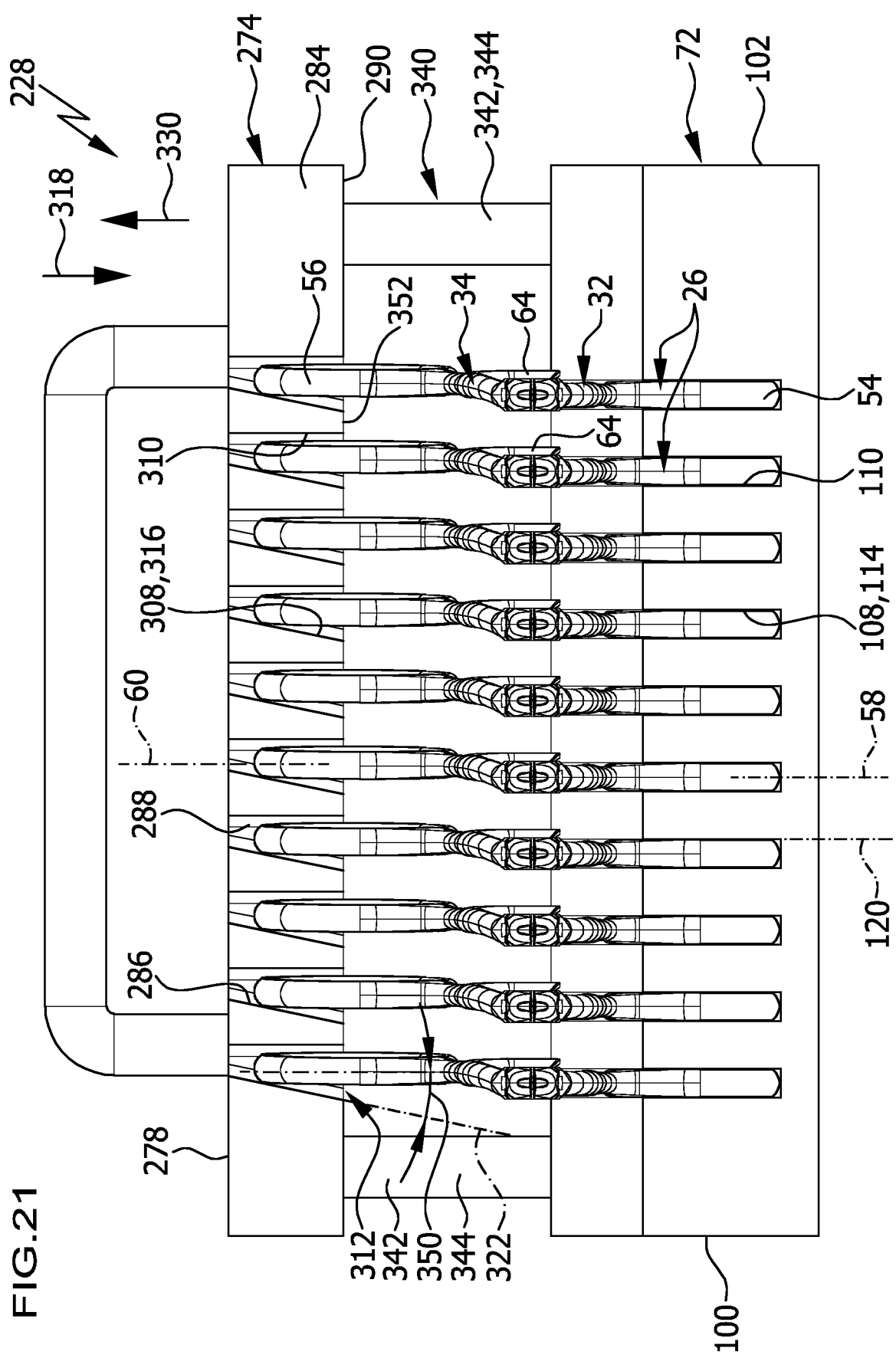
Figure 22:
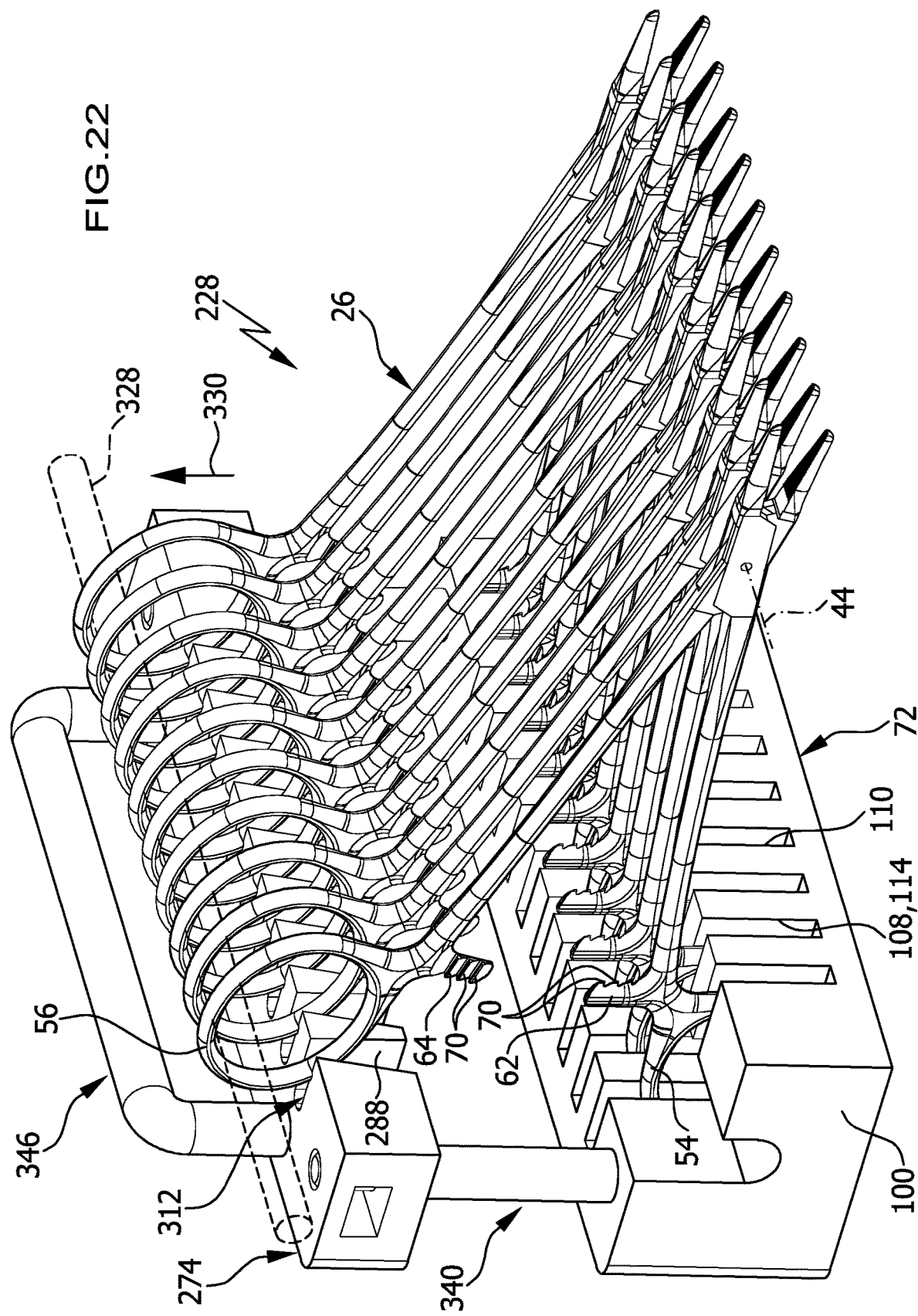
Figure 23:
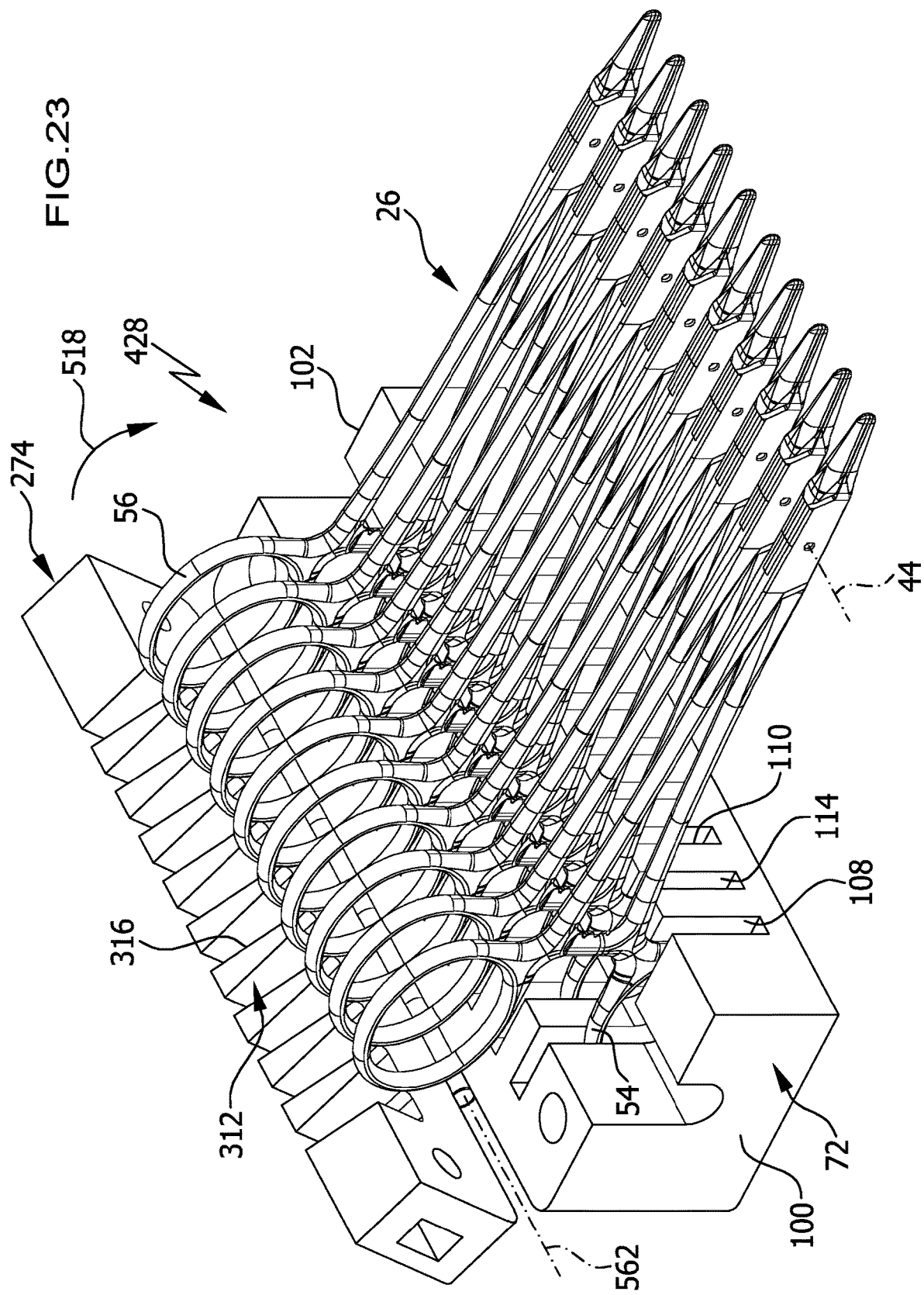
Figure 24:
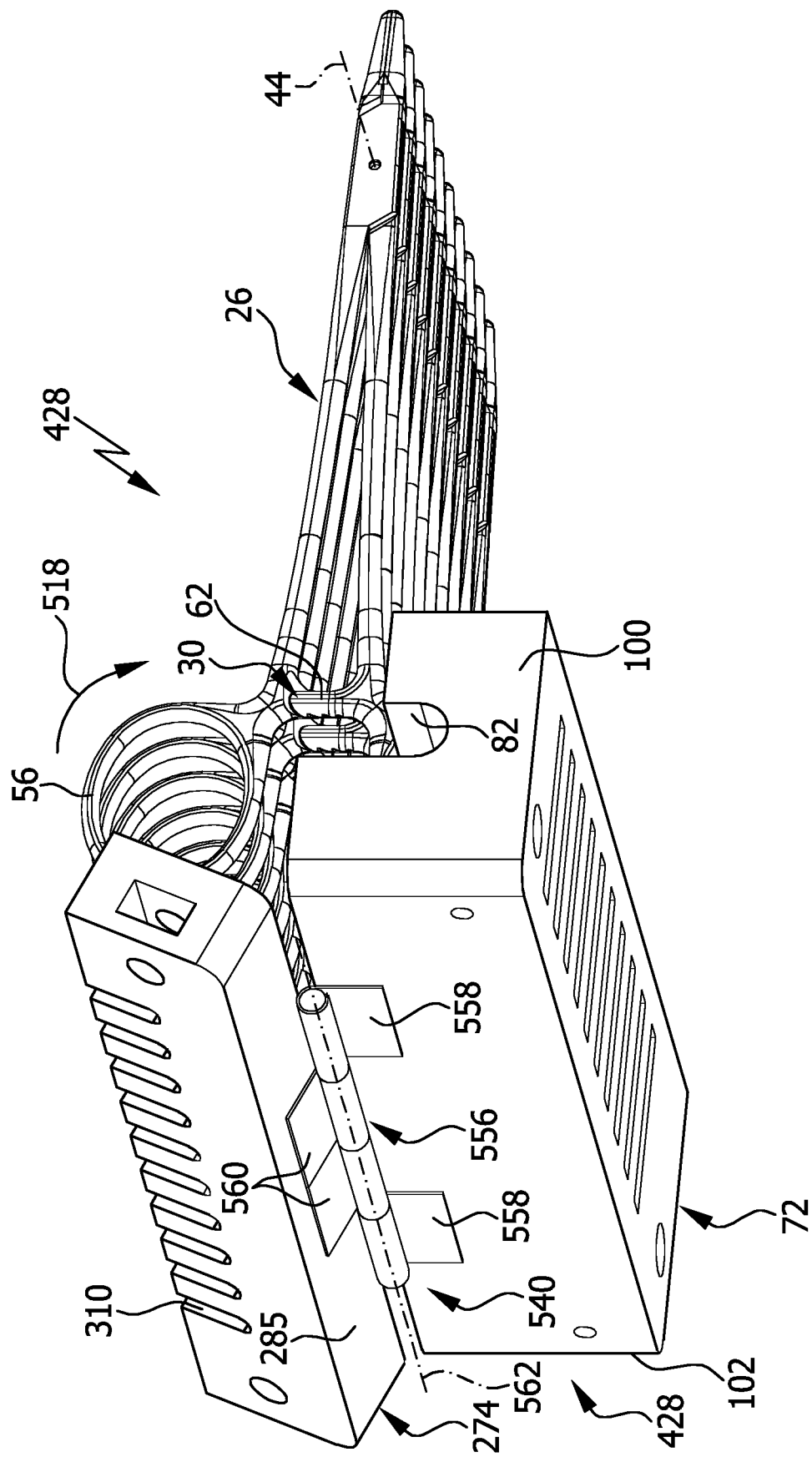
Figure 25:
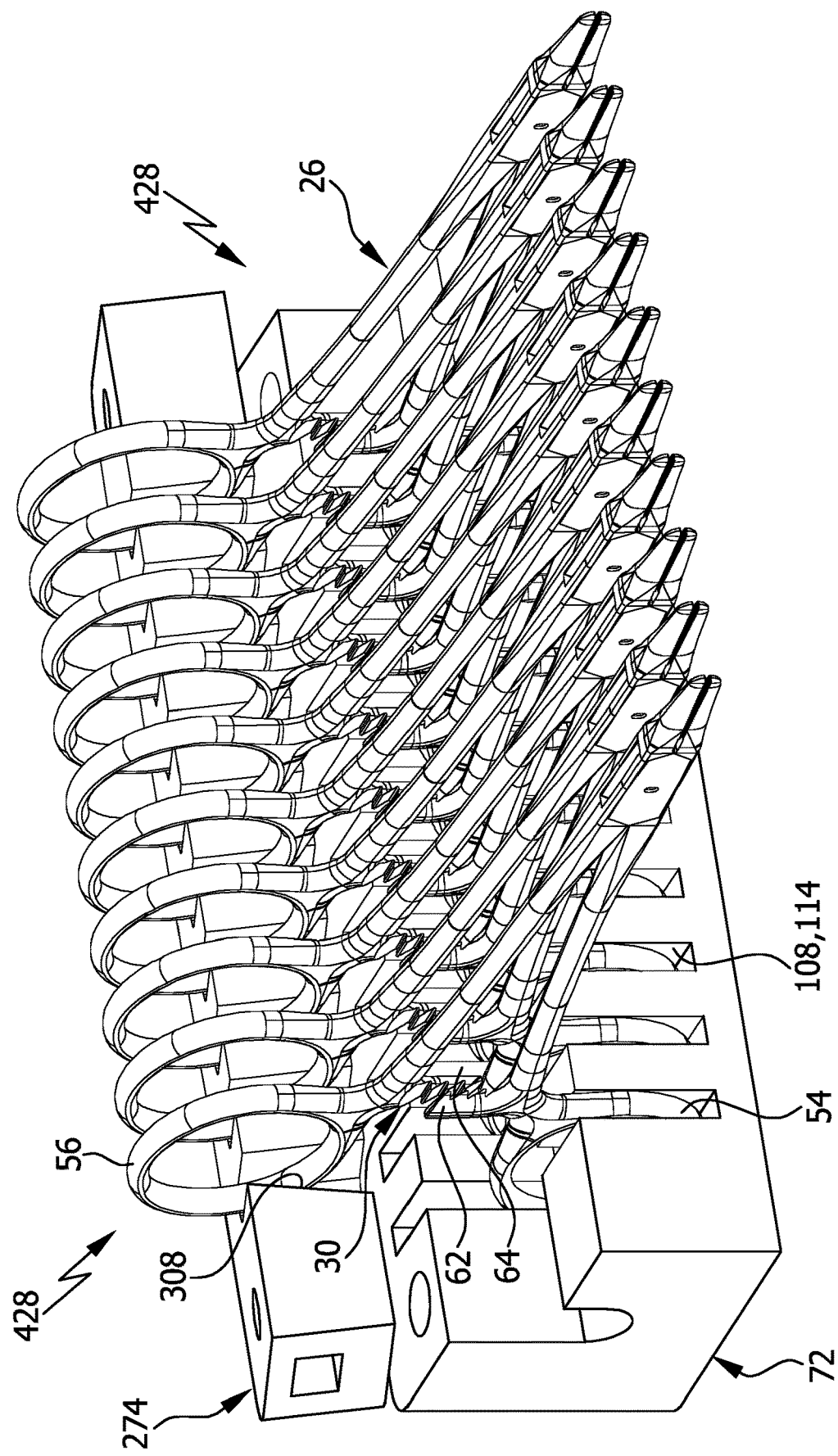
Figure 26:
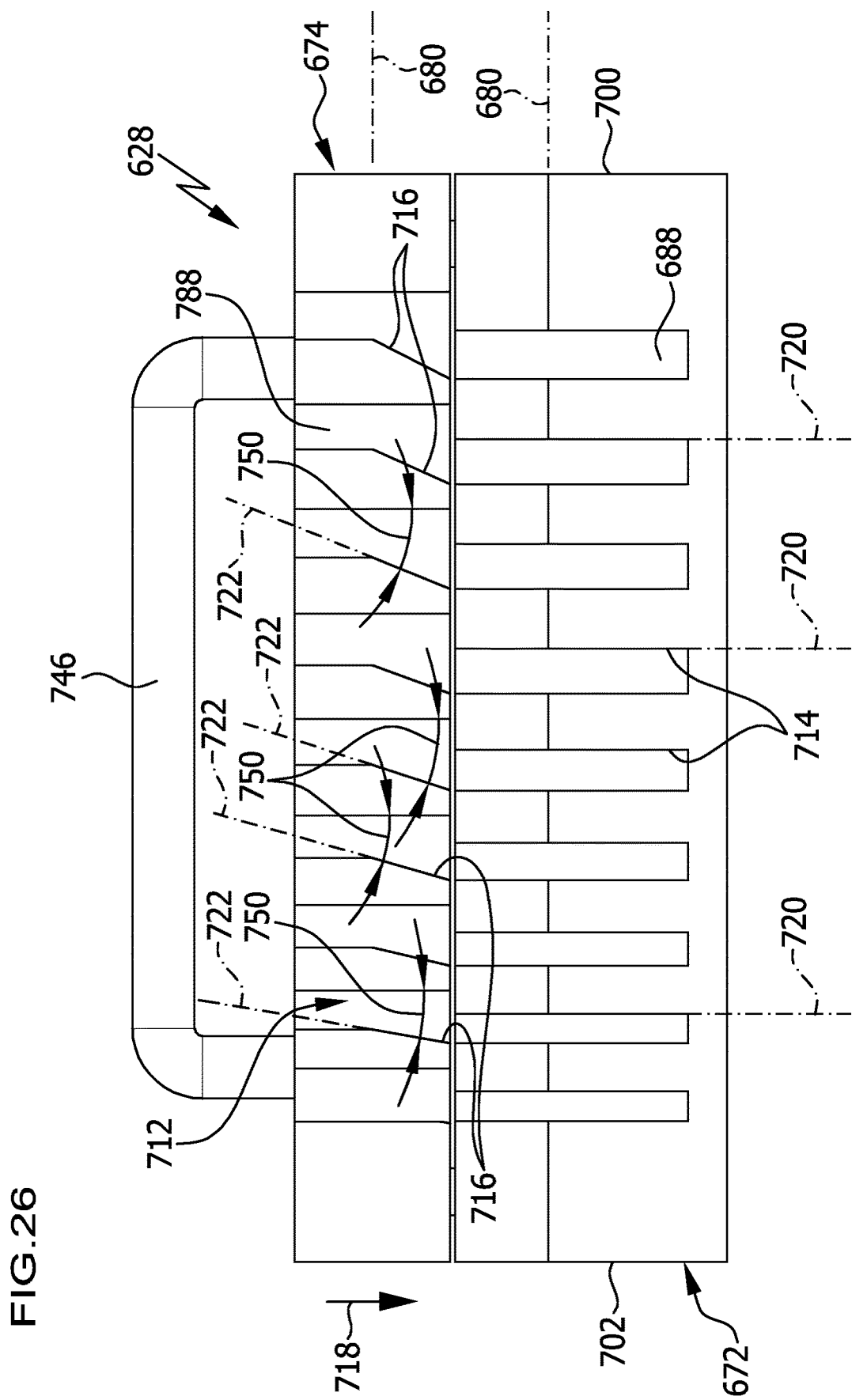
Figure 27:
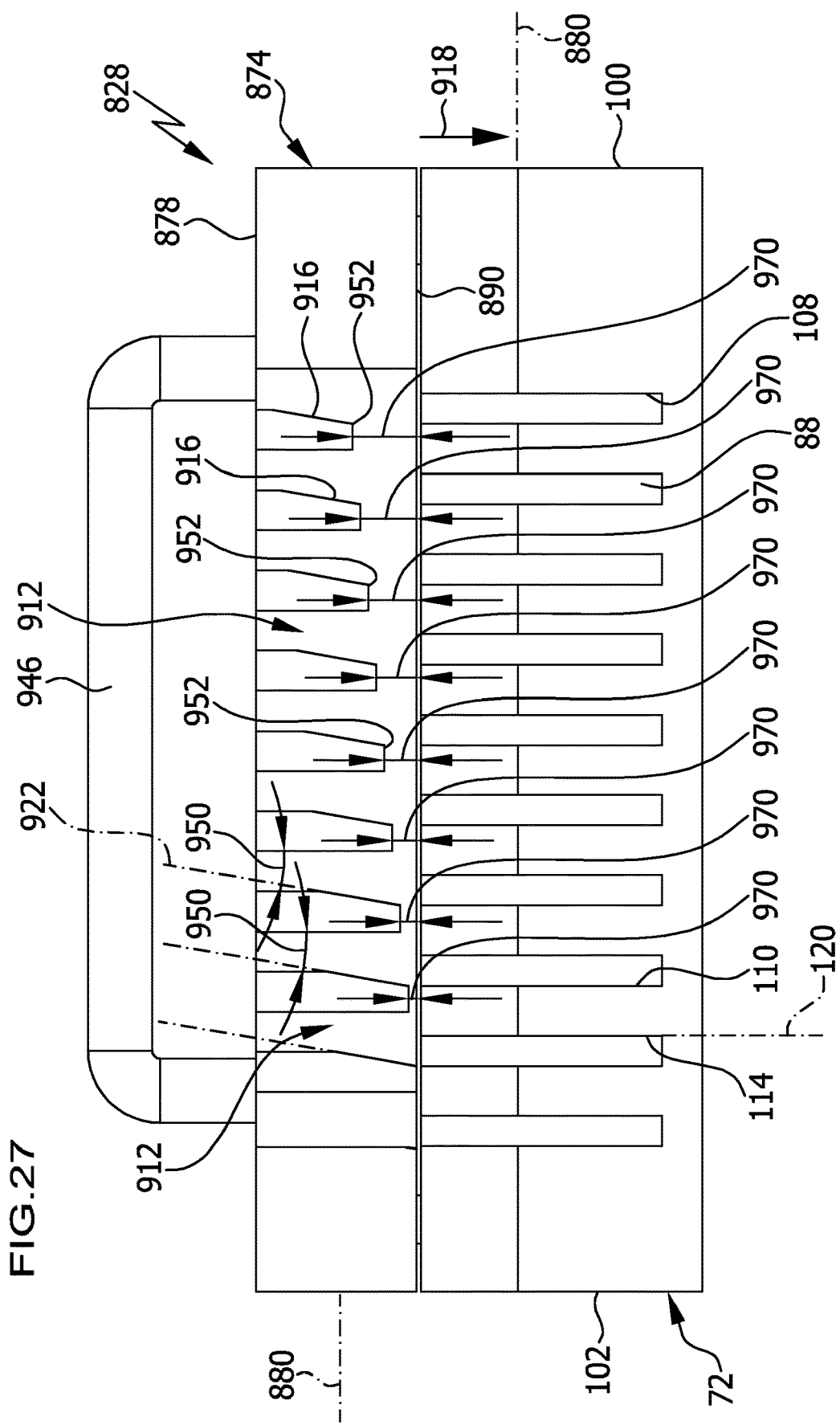

The foregoing summary and the following description may be better understood in conjunction with the drawing figures, of which:

FIG. 1: shows a perspective total view of an embodiment of a sieve basket with two embodiments of unlocking apparatuses accommodated in the sieve basket with ring instruments placed therein;

FIG. 2: shows a plan view of an embodiment of an unlocking apparatus with ring instruments accommodated therein;

FIG. 3: shows a cut view along line 3-3 in FIG. 2;

FIG. 4: shows a perspective view of the unlocking apparatus from FIGS. 2 and 3;

FIG. 5: shows a view of the unlocking apparatus similar to FIG. 2, wherein the receiving body and the unlocking body are moved relative to one another somewhat in the actuating direction;

FIG. 6: shows a perspective view of the arrangement from FIG. 5;

FIG. 7: shows an enlarged sectional view of region A from FIG. 6;

FIG. 8: shows a perspective view of the unlocking apparatus from FIGS. 2 to 7 with opened ring instruments;

FIG. 9: shows a plan view of the arrangement from FIG. 8 from above;

FIG. 10: shows a perspective view of a receiving body of an unlocking apparatus;

FIG. 11: shows a view of the arrangement from FIG. 10 in the direction of arrow B;

FIG. 12: shows a view of the arrangement from FIG. 10 in the direction of arrow C;

FIG. 13: shows a cut view along line 13-13 in FIG. 12;

FIG. 14: shows a cut view along line 14-14 in FIG. 12;

FIG. 15: shows a perspective total view of a further embodiment of an unlocking apparatus with ring instruments accommodated therein;

FIG. 16: shows a view of the arrangement from FIG. 15 in the direction of arrow D from above;

FIG. 17: shows a view of the arrangement from FIG. 16 in the direction of arrow E from the front;

FIG. 18: shows a view similar to FIG. 15, the unlocking body being moved somewhat toward the receiving body to unlock the ring instruments;

FIG. 19: shows an enlarged partial view of region F from FIG. 18;

FIG. 20: shows a view of the arrangement from FIG. 18, the unlocking body and the receiving body being brought closer to one another;

FIG. 21: shows a view of the arrangement from FIG. 18 in the direction of arrow G from the front;

FIG. 22: shows a view of the arrangement from FIG. 15 with ring instruments open after unlocking;

FIG. 23: shows a schematic perspective total view of a further embodiment of an unlocking apparatus with ring instruments accommodated therein before being unlocked;

FIG. 24: shows a further perspective view of the arrangement from FIG. 23;

FIG. 25: shows a schematic view of the arrangement from FIGS. 23 and 24 upon unlocking the ring instruments;

FIG. 26: shows a schematic view of a further embodiment of an unlocking apparatus; and FIG. 27: shows a schematic view of a further embodiment of an unlocking apparatus.

DETAILED DESCRIPTION

Although the present disclosure is illustrated and described herein with reference to specific embodiments, the disclosure is not intended to be limited to the details shown. Rather, various modifications may be made in the details without departing from the disclosure.

The present disclosure relates to an unlocking apparatus for unlocking locking devices of at least two medical ring instruments, said locking devices comprising cooperating locking elements, wherein the cooperating locking elements are in force-locking and/or positive-locking engagement in a locked position and are out of engagement in an unlocked position, wherein the ring instruments each comprise a first branch with a first distal end and a first proximal end and each comprise a second branch with a second distal end and a second proximal end, wherein the first branch and the second branch of each ring instrument are mounted on one another so as to be pivotable about a pivot axis, wherein a first ring is arranged or formed on the first proximal end of the first branch of each ring instrument and wherein a second ring is arranged or formed on the second proximal end of the second branch of each ring instrument, wherein each first ring defines a first ring plane and wherein each second ring defines a second ring plane, wherein the first ring plane and the second ring plane of each ring instrument run in parallel or substantially in parallel to one another, wherein the pivot axis runs transversely, in particular perpendicularly, to the first ring plane and/or to the second ring plane, wherein the unlocking apparatus comprises a receiving body with at least two ring receptacles for accommodating the first rings of the at least two ring instruments, wherein the unlocking apparatus comprises an unlocking body with at least two unlocking elements cooperating with the second rings of the at least two ring instruments, wherein the unlocking body and the receiving body are arranged so as to be movable relative to one another in an actuating direction in such a way that the at least two unlocking elements thereby engage on the second rings and move same relative to the first rings in an unlocking direction transversely, in particular perpendicularly, to the first ring plane and to the second ring plane for transferring the locking devices of the at least two ring instruments from the locked position into the unlocked position.

With such an unlocking apparatus, it is possible, in particular, to unlock two or more, conceivably any number, of ring instruments in a simple manner, namely by moving the unlocking body and the receiving body relative to one another in the actuating direction. This movement causes the second rings to be moved relative to the first rings of the ring instruments in the described manner, the locking elements of the locking devices that are in engagement in the locked position thereby being brought out of engagement. In particular, it is thus possible to unlock two or more ring instruments simultaneously. The unlocking apparatus thus assists a user, who until now had to unlock the ring instruments individually by hand. Using the unlocking apparatus, in particular, the user can place the first rings of all ring instruments into a respective one of the ring receptacles of the receiving body and then with the unlocking body, by relative movement to the receiving body in the actuating direction, move the second rings of the ring instruments relative to the first rings of the ring instruments in such a way that the locking elements are brought out of engagement and thus the ring instruments are transferred from the locked position into the unlocked position. Unlike in manual unlocking of ring instruments when a user must reach with thumb and index finger into the two rings of the ring instrument in order transfer the locking device from the locked position into the unlocked position, in the case of the proposed unlocking apparatus, the user must merely move the receiving body and the unlocking body relative to one another in the actuating direction in order to unlock two or more ring instruments.

It is favorable if the receiving body and the unlocking body are coupled for guiding a movement relative to one another. For example, they may be displaceably held on one another by way of a tongue-and-groove connection. Thus, in particular, the actuating direction of the unlocking apparatus can thus be specified to a user in a simple manner.

It is favorable if the unlocking apparatus comprises a linear movement guidance device and/or a pivotal movement guidance device. The linear movement guidance device enables, in particular, the guidance of a linear movement of the receiving body and the unlocking body relative to one another. The pivotal movement guidance device enables, in particular, the guidance of a pivotal movement about a pivot axis of the receiving body and the unlocking body relative to one another.

A pivotal movement of the receiving body and the unlocking body relative to one another can, in particular, be guided in a simple manner if the pivotal movement guidance device comprises a pivot bearing. The unlocking body and the receiving body may, in particular, be movably coupled to one another by the pivot bearing. The pivot bearing may be configured, in particular, in the form of a hinge joint.

It is advantageous if the linear movement guidance device comprises at least one rectilinearly configured guidance element. In particular, the at least one guidance element may be configured in the form of a guide rod. The linear movement guidance device may also be configured, e.g., in the form of a tongue-and-groove connection in order to guide a linear or rectilinear movement of the receiving body and the unlocking body relative to one another. In particular, two or more guidance elements may be provided.

The at least one guidance element is preferably arranged or formed on the unlocking body or on the receiving body and is displaceably accommodated in a guidance element receptacle on the other body. For example, the guide rod may be arranged on the unlocking body, engage into a guidance element receptacle on the receiving body, and be displaceable therein. Correspondingly, the guidance element may also be arranged or formed on the receiving body and be displaceably accommodated in a guidance element receptacle on the unlocking body.

In order to be able to unlock as many ring instruments as possible with the unlocking apparatus, it is advantageous if the receiving body comprises a plurality of ring receptacles, if a first ring of a ring instrument is at least partially, in particular completely, insertable in each of the plurality of ring receptacles and if the unlocking body comprises a plurality of unlocking elements. This configuration makes it possible, in particular, for a user to simultaneously or successively unlock a plurality of ring instruments with the unlocking apparatus.

A number of ring receptacles of the receiving body preferably corresponds to a number of unlocking elements of the unlocking body. It is thus ensured that all ring instruments that can be placed in the ring receptacles of the receiving body are also able to be unlocked with the unlocking apparatus in an unlocking operation.

In order to, in particular, be able to quickly recognize and verify a number of ring instruments, it is advantageous if the at least two ring receptacles of the receiving body and/or the at least two unlocking elements are consecutively numbered. A user can thus, for example when the unlocking apparatus is accommodated in a sieve basket, quickly recognize whether all instruments are present.

The unlocking apparatus can be configured in a simple manner if each of the at least two ring receptacles is configured in the form of a receiving slot or a receiving groove.

In accordance with a further preferred embodiment, provision may be made that each of the at least two ring receptacles has an abutment surface for an accommodated first ring and that the abutment surface runs in parallel or substantially in parallel to the first ring plane. When unlocking, i.e., upon a movement of the unlocking body and the receiving body relative to one another in the actuating direction, the first rings of the ring instruments abut against the abutment surfaces of the ring receptacles, such that the second rings of the ring elements can be moved relative to the first rings in the described manner by means of the unlocking elements in order to unlock the locking devices of the ring instruments.

Furthermore, it is advantageous if the at least two unlocking elements each have an unlocking face on which the second rings abut against and/or slide on one another upon a movement of the unlocking body and the receiving body relative to one another in the actuating direction. This design of the at least two unlocking elements enables a simple cooperation thereof with the second rings in order to unlock the locking devices of the ring instruments. The unlocking faces may be configured, in particular, as bearing surfaces and/or as sliding surfaces, which can also be referred to as run-up slopes.

It is favorable if each abutment surface defines an abutment plane, if each unlocking face defines an unlocking plane, and if a distance between the abutment plane and the unlocking plane of ring receptacles and unlocking elements, which are associated with one another for releasing the locking device of one of the at least two ring elements, decreases upon moving the unlocking body and the receiving body relative to one another in the actuating direction. In other words, as a result of the reduction of the distance of the abutment plane and the unlocking plane upon the movement of the unlocking body and the receiving body relative to one another, the first and second rings of each ring instrument can be displaced relative to one another in parallel, the locking devices of the ring instruments thereby being able to be transferred from the locked position into the unlocked position in a simple manner.

It is favorable if the receiving body has a longitudinal perforation and If the longitudinal perforation passes through the at least two ring receptacles. This design makes it possible, in particular, to insert, e.g., a holding member into the longitudinal perforation when the ring instruments are accommodated with their first rings in the ring receptacles of the receiving body. Thus, all first rings can be strung on the holding member in a simple manner.

The receiving body can be configured in a simple manner if the longitudinal perforation is configured in the form of a bore. It may also be configured in the form of a groove or a slot on the receiving body.

In order to be able to jointly handle the first rings of the ring instruments in the described manner, it is advantageous if the unlocking apparatus comprises a holding member, which is to accommodated in the longitudinal perforation in a holding position. If the first rings of the ring instruments are already inserted in the ring receptacles, then all first rings can be strung on the holding member. The unlocking apparatus may optionally also comprise a further holding member on which the second rings of the ring instruments can be strung. Both holding members may also be coupled to one another. For example, a U-shaped arrangement can thus be formed in which the two holding members form the legs of the arrangement on which the first and second rings of all ring instruments are strung. With such an arrangement, which is also referred to as a stringer, the ring instruments can be held in an opened position in a defined manner. A spacing of the holding members thereby defines how far the ring instruments are opened.

The holding member is favorably of rod-shaped configuration. Such a holding member can be produced and handled in a simple manner.

In order to make the production of the unlocking apparatus as simple as possible, it is advantageous if the receiving body is of cuboidal or substantially cuboidal configuration and defines a longitudinal direction and if the longitudinal direction runs transversely, in particular perpendicularly, to the ring receptacles. Cuboidal in this sense means, in particular, a basic shape or original shape of the receiving body, which to form the ring receptacles and, in particular, the longitudinal perforation may be processed in such a way that is has an L-shape or a U-shape in a cross section transverse to the longitudinal direction.

The unlocking of the ring instruments can be simplified, in particular, by the longitudinal direction running transversely to the abutment surfaces.

The rings of the ring instruments can be strung on a holding member in a simple manner if the longitudinal perforation extends in parallel to the longitudinal direction.

It is advantageous if the actuating direction runs in parallel to the longitudinal direction. To unlock the ring instruments, the receiving body and the unlocking body must thus be moved relative to one another only in parallel to the longitudinal direction of the receiving body.

In accordance with a further preferred embodiment, provision may be made that the receiving body and the unlocking body are movable in a direction transverse, in particular perpendicular, to the at least two ring receptacles, in particular transverse to the first ring planes of the at least two ring instruments, for transferring the locking devices of the at least two ring instruments from the locked position into the unlocked position. In other words, in this embodiment, the receiving body and the unlocking body are moved relative to one another in a direction transverse to the ring receptacles. In particular, it may be the longitudinal direction of the receiving body.

The structure of the unlocking apparatus can be simplified, in particular, by the receiving body and the unlocking body being of identical configuration. In other words, the unlocking apparatus comprises two of the preferred embodiments of receiving bodies described above. The one receiving body accommodates the first rings of the ring instruments in its ring receptacles. The second receiving body accommodates the second rings of the ring instruments. To unlock the ring instruments, the two receiving bodies can then be moved relative to one another in parallel to the longitudinal directions defined thereby.

It is favorable if the abutment surfaces of the unlocking body configured identically to the receiving body define the unlocking faces. This makes it possible in a simple manner to apply the necessary forces to unlock the locking devices of the ring instruments.

Furthermore, it is favorable if the ring receptacles of the receiving body and the ring receptacles of the unlocking body configured identically to the receiving body are arranged mirror-symmetrically opposite one another for accommodating the first rings of the at least two ring instruments on the one hand and the second rings of the at least two ring instruments on the other hand. This arrangement of the two identical receiving bodies enables a simple insertion of the ring instruments with their rings into the respective ring receptacles.

The ring receptacles preferably extend from a receiving body top side to a receiving body bottom side. This design has the advantage, in particular, that the unlocking apparatus is easily cleanable. The ring receptacles can thus be completely rinsed. In particular, they thus do not hinder a cleaning of the ring instruments accommodated in the unlocking apparatus, for example when they are washed in a washing machine and then sterilized with hot steam in a hot steam sterilization device.

In accordance with a further preferred embodiment, provision may be made that to open the ring instruments after the transfer from the locked position into the unlocked position, the receiving body and the unlocking body are movable in an opening direction by pivoting the first and second rings away from one another, said opening direction running transversely, in particular perpendicularly, to the actuating direction. In other words, the receiving body and the unlocking body can be moved away from one another in the opening direction. Upon this movement, the ring instruments are opened by pivoting their two branches relative to one another about the pivot axes of the ring instruments. Thus, not only can two or more instruments be unlocked in a simple manner with the unlocking apparatus, but they can also be opened, which is advantageous for an optimal cleaning and reprocessing of the ring instruments.

In accordance with a further preferred embodiment, provision may be made that the receiving body and the unlocking body are movable in the actuating direction in parallel or substantially in parallel to the at least two ring receptacles, in particular in parallel to the first ring planes of the at least two ring instruments, for transferring the locking devices of the at least two ring instruments from the locked position into the unlocked position. Such a movement can be achieved, in particular, by the receiving body and the unlocking body first being somewhat at a distance from one another and then being moved toward one another to unlock the ring instruments. To unlock the ring instruments, the first rings can thus, for example, be placed in the ring receptacles of the receiving body after the unlocking body has first been moved away from the receiving body. To unlock the ring instruments, the unlocking body is then moved in the direction toward the receiving body. The unlocking elements of the unlocking body thereby cooperate in the described manner with the second rings of the ring instruments in order to move same relative to the first rings in the unlocking direction to transfer the locking devices of the ring instruments from the locked position into the unlocked position.

It is favorable if the actuating direction runs in an actuating plane, which extends in parallel to the first and/or second ring planes. The actuating direction does not necessarily have to be linear. It may also define a curved path.

It is favorable if the receiving body and the unlocking body are arranged or formed so as to be displaceable relative to one another in the actuating plane and/or pivotable about a pivot axis running transversely, in particular perpendicularly, to the first and/or second ring planes. This design makes it possible, in particular, to move the receiving body and the unlocking body relative to one another along a rectilinear path, along a circular path, or through a superimposition of a rectilinear movement and a pivotal movement in order to unlock the ring instruments.

The unlocking apparatus can be configured in a simple manner if the actuating direction runs transversely, in particular perpendicularly, to the longitudinal direction of the receiving body.

It is advantageous if the second rings each abut against and slide on a respective unlocking face of the unlocking body upon a movement of the unlocking body and the receiving body relative to one another in the actuating direction. This design makes it possible, in particular, to move the second rings of the ring instruments in a defined manner. A movement in the unlocking direction may thus depend, in particular, on how far toward one another the unlocking body and the receiving body are already moved.

Unlocking planes defined by the unlocking faces are favorably inclined relative to the associated abutment planes by an angle of inclination. This design makes it possible, in particular, for the second rings to slide on the unlocking faces in a simple manner upon a movement of the unlocking body and the receiving body in the actuating direction toward one another. As a result of this design of the actuating elements, an actuating force that is applied by a user in the actuating direction can thus be redirected in the unlocking direction in order to move the first rings and the second rings relative to one another in the unlocking direction to transfer the locking devices from the locked position into the unlocked position.

The locking devices of the ring instruments can be unlocked in a simple manner, in particular, if the angle of inclination is in a range of about 10° to about 50°.

The angle of inclination of all unlocking faces is preferably identical. This design makes it possible, in particular, to configure the unlocking apparatus in such a way that all ring instruments can be unlocked simultaneously.

Furthermore, it may be advantageous if the angles of inclination of the unlocking faces of the unlocking body are different. It can thereby be achieved, in particular, that the ring instruments are unlocked not simultaneously but rather one after the other, i.e., successively. The greater the angle of inclination is, the sooner the ring instruments are unlocked. Upon a movement of the unlocking body and the receiving body toward one another, those ring instruments that cooperate with unlocking elements that have the greatest angles of inclination of the unlocking faces are unlocked first.

The angles of inclination of adjacent unlocking faces preferably increase successively. Ring instruments accommodated adjacent to one another in the unlocking apparatus can thus be opened, namely by a single movement of the unlocking body and the receiving body toward one another. In particular, the angles of inclination of adjacent unlocking faces may increase by an angle of change in a range of about 1° to about 10°. In particular, the angle of change may be about 2° to about 3°. Furthermore, the angle of change may also depend on a number of ring receptacles on the receiving body. The greater the number of ring receptacles, the smaller the angle of change is. It can thus be ensured that all ring instruments can be unlocked in a simple manner with the unlocking apparatus.

Moreover, it may be advantageous if a distance of ends of the unlocking faces pointing in the direction toward the receiving body from an unlocking body bottom side that points in the direction toward the receiving body is identical. This design makes it possible, in particular, for all unlocking elements to simultaneously come into contact with second rings of the ring instruments and cooperate therewith to unlock the locking devices. In particular, this is independent of whether the angles of inclination of all unlocking faces are Identical or different. If in this case the angles of inclination are identical, the rings instruments can be unlocked simultaneously. If the angles of inclination of the unlocking faces are different, the ring instruments can be unlocked successively in the described manner.

Furthermore, it may be favorable if a distance of ends of the unlocking faces pointing in the direction toward the receiving body from an unlocking body bottom side that points in the direction toward the receiving body is different. This design has the result, in particular, that upon a movement of the unlocking body and the receiving body toward one another, the second rings of the ring instruments are able to, not simultaneously, but rather successively come into contact with the unlocking faces of the unlocking elements and cooperate therewith to unlock the locking devices. The ring instruments thus can thus still not be unlocked simultaneously but rather successively, in particular when the angles of inclination of all unlocking faces are identical.

In order to enable a successive unlocking of the plurality of ring elements with the unlocking apparatus, it is favorable if the distance of adjacent unlocking faces from the unlocking body bottom side successively increases. In particular, the distance may increase linearly.

In accordance with a further preferred embodiment, provision may be made that the receiving body comprises a coupling device for coupling to a sieve basket in a force-locking and/or positive-locking manner in a coupling position. The coupling device enables, in particular, a defined and secure arrangement of the receiving body in the sieve basket. In particular, it can thus be coupled to the sieve basket in an immovable manner. In this case, to handle the unlocking apparatus, a user can then move the unlocking body with one hand and hold the sieve basket with the other hand. The user therefore does not have to grab directly on the receiving body in order to unlock the ring instruments.

In accordance with a further preferred embodiment, provision may be made that the unlocking apparatus is configured to simultaneously release all locking devices of the ring instruments accommodated in the unlocking apparatus upon a movement of the unlocking body and the receiving body relative to one another in the actuating direction. The simultaneous release or unlocking of all locking devices is possible with different embodiments that have already been described above.

Furthermore, it may be advantageous if the unlocking apparatus is configured to successively release all locking devices of the instruments accommodated in the unlocking apparatus upon a movement of the unlocking body and the receiving body relative to one another in the actuating direction. In particular, this can be achieved by varying a distance of ends of the unlocking faces pointing in the direction toward the receiving body from an unlocking body bottom side, as has already been described above, or by varying the angle of inclination of the unlocking faces of the unlocking body. This has also been described in detail above.

So that the unlocking apparatus can remain in a sieve basket during a reprocessing of the ring instruments, it is advantageous if the unlocking apparatus is made of one or more materials that is/are sterilizable with hot steam. In particular, the materials may be plastics or metals, for example polyetheretherketone (PEEK) or an instrument steel. In particular, the receiving body and the unlocking body can be made from a plastic in a simple manner. The described holding members and the at least one guidance element may be made, in particular, of a metallic material in order to improve a stability of the unlocking apparatus.

It is favorable if a grip element is arranged on the receiving body and/or on the unlocking body for handling the unlocking apparatus. A grip element may be configured, in particular, in the form of a projecting bracket. Grip elements can also be formed by ergonomically shaping the receiving body and the unlocking body, for example by providing grip recesses for individual or a plurality of fingers of a hand of a user. A grip element may also be configured, in particular, in the form of an actuating lever, which is rigidly or movably coupled to the unlocking body in order to move same relative to the receiving body. Such an actuating lever may be configured, in particular, in the form of an eccentric lever in order to minimize the effort required of a user to actuate the unlocking apparatus for unlocking the ring instruments accommodated therein.

The present disclosure further relates to a sieve basket with a receiving space for accommodating surgical instruments, wherein an unlocking apparatus for unlocking locking devices of at least two medical ring instruments is arranged in the receiving space, said locking devices comprising cooperating locking elements, wherein the cooperating locking elements are in force-locking and/or positive-locking engagement in a locked position and are out of engagement in an unlocked position, wherein the ring instruments each comprise a first branch with a first distal end and a first proximal end and each comprise a second branch with a second distal end and a second proximal end, wherein the first branch and the second branch of each ring instrument are mounted on one another so as to be pivotable about a pivot axis, wherein a first ring is arranged or formed on the first proximal end of the first branch of each ring instrument and wherein a second ring is arranged or formed on the second proximal end of the second branch of each ring instrument, wherein each first ring defines a first ring plane and wherein each second ring defines a second ring plane, wherein the first ring plane and the second ring plane of each ring instrument run in parallel or substantially in parallel to one another, wherein the pivot axis runs transversely, in particular perpendicularly, to the first ring plane and/or to the second ring plane, wherein the unlocking apparatus comprises a receiving body with at least two ring receptacles for accommodating the first rings of the at least two ring instruments, wherein the unlocking apparatus comprises an unlocking body with at least two unlocking elements cooperating with the second rings of the at least two ring instruments, wherein the unlocking body and the receiving body are arranged so as to be movable relative to one another in an actuating direction in such a way that the at least two unlocking elements thereby engage on the second rings and move same relative to the first rings in an unlocking direction transversely, in particular perpendicularly, to the first ring plane and to the second ring plane for transferring the locking devices of the at least two ring instruments from the locked position into the unlocked position.

Such a sieve basket has, in particular, the advantages that have already been described above in conjunction with preferred embodiments of unlocking apparatuses. It is further favorable, for example, to arrange an unlocking apparatus in the receiving space in order to increase a clear arrangement of the instruments accommodated in the sieve basket. The instruments can thus, in particular, be arranged discretely ordered in the sieve basket. This also makes it possible to easily verify the completeness of the sieve basket, i.e., in particular whether all instruments used in a surgical procedure are again completely contained in the sieve basket. Moreover, the unlocking of the ring instruments can be carried out in the sieve basket in a simple manner.

It is advantageous if the sieve basket comprises a sieve basket base and sieve basket walls extending transversely, in particular perpendicularly, away from the sieve basket base, if the sieve basket base and the sieve basket walls delimit the receiving space, and if the sieve basket base and/or the sieve basket walls are provided with a plurality of perforations. Perforations in this sense may be, in particular, openings of any kind. Their shape and size may be identical or vary. For example, the sieve basket base and the sieve basket walls may be of plate-shaped configuration and have perforations that are circular or polygonal in cross section. The perforations can be used, in particular, to temporarily or permanently couple, in particular, the receiving body to the sieve basket.

The coupling device of the receiving body is favorably configured to be brought into force-locking and/or positive-locking engagement with perforations of the sieve basket base and/or of the sieve basket walls in the coupling position. For example, bracket-shaped projections may be formed on the receiving body, which are hooked into the perforations. Elastic projections made of a plastic are also conceivable, which are clampingly held in the perforations in the coupling position.

Furthermore, the use of one of the unlocking apparatuses described above is proposed for simultaneously or successively bringing cooperating locking elements of locking devices of at least two medical ring instruments out of engagement.

For this purpose, as already described, first rings of the ring instruments can be inserted into the ring receptacles of the receiving body and then moved relative to the receiving body in the actuating direction to unlock the locking devices of the unlocking body.

An embodiment of a sieve basket 10 with a receiving space 12 is schematically depicted in FIG. 1.

The sieve basket 10 comprises a sieve basket base 14 and sieve basket walls 16, 18, 20, and 22 extending transversely away from the sieve basket base 14. The sieve basket base 14 and the sieve basket walls 16, 18, 20, and 22 delimit the receiving space 12.

The sieve basket walls 16 and 20 are oriented in parallel to one another in the embodiment of the sieve basket 10 depicted in FIG. 1. The sieve basket walls 18 and 22 are also oriented in parallel to one another.

The sieve basket base 14 and the sieve basket walls 16, 18, 20, and 22 are each provided with a plurality of perforations 24. They are configured in the form of square openings and are arranged in a regular pattern, namely a two-dimensional grid.

The sieve basket 10 serves to accommodate surgical instruments, for example the ring instruments 26 that are schematically depicted purely as an example in FIG. 1. The ring instruments 26 are configured in the form of needle holders. They may alternatively also be configured in the form of clamps or other instruments.

The ring instruments 26 are accommodated in the sieve basket 10 in an ordered manner, as schematically depicted in FIG. 1. Serving this purpose are two identically configured unlocking apparatuses 28, the structure and functioning of which are explained in more detail in the following in conjunction with FIGS. 2 to 14.

The embodiment of the unlocking apparatus 28 depicted in the Figures serves to unlock two or more ring instruments 26 that comprise locking devices 30. Furthermore, the ring instruments 26 comprise a first branch 32 and a second branch 34. The first branch 32 has a first distal end 36 and a first proximal end 38. The second branch 34 has a second distal end 40 and a second proximal end 42.

The two branches 32 and 34 are mounted on one another so as to be pivotable about a pivot axis 44.

In the case of the ring instruments 26 depicted in FIGS. 1 to 8, a box connection 46 is formed in the region of the pivot axis 44.

The distal ends 36 and 40 are configured in the form of clamping jaws 48 and 50.

The branches 32 and 34 extend in a rod-like manner and substantially rectilinearly from the connection region 52 defined by the box connection 46 up to the proximal ends 38 and 42.

A first ring 54 is arranged on the first proximal end 38. A second ring 56 is arranged on the second proximal end 42.

The first ring 54 defines a first ring plane 58, the second ring 56 a second ring plane 60. The first ring plane 58 and the second ring plane 60 of the ring instrument 26 extend in parallel to one another.

In the embodiment of the ring instrument 26 depicted in the Figures, the pivot axis 44 runs transversely, namely perpendicularly, to the first ring plane 58 and to the second ring plane 60.

The locking device 30 comprises two identical locking elements 62 and 64, which are each arranged or formed near the rings 54 and 56, respectively, protruding from the proximal ends 38 and 40, respectively, pointing toward one another.

The locking elements 62 and 64 each comprise a respective toothing 66 and 68. The toothings 66 and 68 each comprise three undercut locking teeth 70, which are each directed toward the locking teeth 70 of the respective other toothing 66 and 68.

In a locked position of the ring instruments 26 schematically depicted in FIGS. 1 to 4, the cooperating locking elements 62 and 64 are in engagement by the locking teeth 70 of the toothings 66 and 68 interengaging.

The locking elements 62 and 64 are configured in such a way that the ring instruments 26 interengage upon closing same, i.e., when the rings 54 and 56 are moved toward one another by pivoting the branches 32 and 34. The ring instruments 26 can be locked by the three provided locking teeth 70 in three positions at different distances against the distal ends 36 and 40 and the rings 54 and 56 against being opened, i.e., moved away from one another. In the locked position, the locking elements 62 and 64 are in force-locking and/or positive-locking engagement.

In order to transfer the ring instruments 26 from the locked position into an unlocked position in which the locking elements 62 and 64 are out of engagement, the proximal ends 38 and 42 must merely be moved somewhat toward one another and then the locking elements 62 and 64 somewhat away from one another in a direction parallel to the pivot axis 44 in order to bring the toothings 66 and 68 out of engagement. A user can perform this unlocking, for example, by hand by reaching with the thumb into the first ring 54 and with the index finger into the second ring 56. Thus, each ring instrument 26 can be unlocked individually by hand.

The unlocking apparatus 28, by contrast, enables a user to open two or more ring instruments 26, namely at most ten ring instruments 26 in the case of the embodiment of the unlocking apparatus 28 depicted in FIGS. 1 to 14, in a single operation, namely simultaneously. This is made possible due to the particular structure of the unlocking apparatus 28. The latter comprises a receiving body 72 and an unlocking body 74. The receiving body 72 and the unlocking body 74 are of identical configuration in the unlocking apparatus 28.

The structure of the receiving body 72 is explained in more detail in the following in conjunction with FIGS. 10 to 14.

The receiving body 72 is made of a cuboidal base body 76 on which, commencing from the receiving body top side 78, a groove-shaped longitudinal perforation 82 extending in parallel to a longitudinal direction 80 defined by the receiving body 72 is formed.

In the depicted embodiment, a total of ten receiving slots 86 are formed on a longitudinal side 84 extending in parallel to the longitudinal direction 80, each receiving slot 86 forming a ring receptacle 88 for accommodating a first ring 54 of a ring instrument 26.

The receiving slots 86 extend from the receiving body top side 78 to a receiving body bottom side 90 of the receiving body 72. The receiving slots 86 open the receiving body 72 only on the receiving body top side 78, the longitudinal side 84, and the receiving body bottom side 90.

Commencing from the receiving body top side 78, the base body 76 is set back somewhat toward the longitudinal side 84 commencing from the longitudinal perforation 82 and defines a side surface 92 that is interrupted by the receiving slots 86. A distance 94 between the side surface 92 and the receiving body bottom side 90 is smaller than a distance 96 of the receiving body top side 78 from the receiving body bottom side 90. In the embodiment depicted in the Figures, the distance 94 is about 70% of the distance 96.

Furthermore, two guidance element receptacles 98 are formed on the receiving body 72, namely in the form of bores that pass through the receiving body 72 from the receiving body top side 78 to the receiving body bottom side 90 and run perpendicularly thereto.

As already mentioned, in this embodiment of the unlocking apparatus 28 the unlocking body 74 is of identical configuration to the receiving body 72. The receiving body 72 and the unlocking body 74 are, as schematically depicted in FIGS. 2 and 4, placed with the longitudinal sides 84 against one another, such that two respective ring receptacles 88 are located opposite one another. The first rings 54 of the ring instruments 26 are placed in the ring receptacles 88 of the receiving body 72, the second rings 56 in the ring receptacles 88 of the unlocking body 74.

The ring receptacles 88 are oriented in parallel to first and second end faces 100 and 102 of the receiving body 72. A distance 104 of the ring receptacle 88 located nearest the first end face 100 is smaller than a distance 106 of the ring receptacle 88 located nearest the second end face 102.

The ring receptacles 88 are delimited by two side surfaces running in parallel to one another, namely by a first side surface 108 that faces in the direction toward the second end face 102 and a second side surface 110 that faces in the direction of the first end face 100.

The ring receptacles 88 of the unlocking body 74 form unlocking elements 112, which cooperate with the second rings 56 of the ring instruments 26.

The ring receptacles 88 of the receiving body 72 have an abutment surface 114 for the first rings 54 accommodated in the ring receptacle 88. The abutment surface 114 is formed by the first side surface 108 and runs in parallel to the first ring plane 58.

The unlocking elements 112 each have an unlocking face 116, which is defined by the first side surface 108 of a ring receptacle 88 on the unlocking body 74. The abutment surfaces 114 each define an abutment plane 120. The unlocking faces 116 define an unlocking plane 122.

In order to unlock the ring instruments 26 placed in the ring receptacles 88 on the receiving body 72 and on the unlocking body 74, the receiving body 72 and the unlocking body 74 are moved relative to one another in an actuating direction 118. The actuating direction is schematically symbolized in FIG. 2 by the arrow 118.

The relative movement of the receiving body 72 and the unlocking body 74 in the actuating direction 118 leads to the second end faces 102 moving away from one another. During this movement, the unlocking elements 112 engage on the second rings 56 and move same relative to the first rings 54 in an unlocking direction symbolized by the arrow 124 transverse, namely perpendicular, to the first ring plane 58 and to the second ring plane 60 in order to transfer the locking devices 30 of the ring instruments 26 from the locked position into the unlocked position.

The second rings 56 each abut against an unlocking face 116 upon the relative movement of the receiving body 72 and the unlocking body 74. As a result of the relative movement, a distance 126 decreases between the abutment plane 120 and the unlocking plane 122 of ring receptacles 88 and unlocking elements 112, which are associated with one another for releasing the locking device 30 of a ring instrument 26, upon moving the unlocking body 74 and the receiving body 72 relative to one another in the actuating direction 118. The first rings 54 and the second rings 56 of the ring instruments 26 are thereby offset from one another somewhat in the longitudinal direction 80, such that the first ring plane 58 and the second ring plane 60, which coincide when the ring instruments 26 that are accommodated in the unlocking apparatus 28 are locked, are moved apart. The distance 126 simultaneously decreases. These effects are schematically depicted in FIG. 5. As a result of this lateral movement of the first rings 54 and the second rings 56, the locking elements 62 and 64 of the locking devices 30 come out of engagement, as is schematically depicted in FIGS. 6 and 7.

The unlocking apparatus 28 may optionally comprise two rod-shaped holding members 128, which in a holding position, as it is schematically depicted in FIG. 8, are accommodated in the longitudinal perforations 82 of the receiving body 72 and the unlocking body 74. Because the longitudinal perforation 82 passes through the ring receptacles 88, the holding members 128 pass through, on the one hand, all first rings 54 and, on the other hand, all second rings 56 of the ring instruments 26.

If the holding members 128 are accommodated in the longitudinal perforations 82, the receiving body 72 and the unlocking body 74 can be moved away from one another in an opening direction, which is symbolized in FIG. 8 by the arrow 130, for opening the ring instruments 26 after the described transfer from the locked position into the unlocked position by pivoting the first and second rings 54 and 56 away from one another about the pivot axis 44. The opening direction 130 runs transversely, namely perpendicularly, to the actuating direction 118.

As described, the actuating direction 118 runs in parallel to the longitudinal direction 80. In the described embodiment of the unlocking apparatus 28, the receiving body 72 and the unlocking body 74 are movable in a direction transverse, namely perpendicular, i.e. in the actuating direction 118, to the ring receptacles 88. The actuating direction 118 is thus running transversely to the first ring planes 58 of the ring instruments 26.

In the described embodiment of the unlocking apparatus 28, a number of ring receptacles 88 of the receiving body 72 corresponds to a number of unlocking elements 112 of the unlocking body 74.

Furthermore, the ring receptacles 88 of the receiving body 72 and the unlocking elements 112 are consecutively numbered. Such a numbering 132 is applied to the respective receiving body top side 80 schematically in FIG. 5, for example by printing, laser marking, or embossing.

As already mentioned, the locking devices 30 of the ring instruments 26 can be simultaneously brought out of engagement by the unlocking apparatus 78 due to its design to unlock the ring instruments 26.

Schematically depicted in FIGS. 15 to 22 and denoted as a whole with the reference numeral 228 is a second embodiment of an unlocking apparatus. This unlocking apparatus 228 is also configured to unlock a plurality of ring instruments 26, the structure of which has already been described in detail above.

The unlocking apparatus 228 comprises a receiving body 72 and an unlocking body 274. The receiving body 72 is configured identically to the receiving body 72 of the unlocking apparatus 28. Reference is therefore made to the above description of the receiving body 72 to avoid repetition.

The unlocking body 274 differs from the receiving body 72 in its structure. The unlocking body 274 is made from a cuboidal base body 276. The base body 276 has an unlocking body top side 278 or an unlocking body bottom side 290. Furthermore, the base body 276 defines a longitudinal direction 280 and has two longitudinal sides 284 and 286 facing away from one another.

The unlocking apparatus 228 further comprises a linear movement guidance device 340, by means of which the receiving body 72 and the unlocking body 274 are coupled to guide a movement relative to one another. The linear movement guidance device 340 comprises two rectilinearly configured guidance elements 342 in the form of guide rods 344. The guide rods 344 are fixedly connected to the unlocking body 274 and project perpendicularly from the unlocking body bottom side 290. The guide rods 344 engage in the guidance element receptacles 98 on the receiving body 72. This enables a guidance of a movement of the unlocking body 274 in an actuating direction, which is symbolized schematically in FIG. 18 by the arrow 318, in the direction toward the receiving body 72.

Arranged on the unlocking body 274 on the unlocking body top side 278 is a grip element 346 in the form of U-shaped holding bracket 348. Legs of the holding bracket 348 running in parallel to one another extend in parallel to the guidance elements 342.

The unlocking body 274 has a plurality of unlocking elements 312. They are configured in the form of ring receptacles 288. The ring receptacles 288 are defined by receiving slots 286 that are formed in the unlocking body 274, namely commencing from the longitudinal side 284. The receiving slots 286 extend from the unlocking body top side 278 to the unlocking body bottom side 290.

The receiving slots 286 are laterally delimited by a first side surface 308 and a second side surface 310. The first side surface 308 faces in the direction of the first end face 100, the second side surface 310 in the direction of the second end face 102. The second side surface 310 runs in parallel to the side surfaces 108 and 110 of the receiving body 72. The first side surface 308 defines an unlocking face 316, which defines an unlocking plane 322. The unlocking faces 316 thus define unlocking planes 322, which are inclined by an angle of inclination 350 relative to the associated abutment planes 120, which are defined by the abutment surfaces 114 of the receiving body 72, such that the ring receptacle 288 on the unlocking body 274 tapers away from the receiving body 72.

In the embodiment of the unlocking apparatus 228 depicted in the Figures, the angle of inclination 350 is in a range of about 10° to about 50°. The angles of inclination 350 of all unlocking faces 316 are identical.

Furthermore, a distance of ends 352 of the unlocking faces 316 pointing in the direction toward the receiving body 72 from the unlocking body bottom side 290, which faces in the direction toward the receiving body 72, is identical. The unlocking faces 316 extend from the unlocking body top side 278 to the unlocking body bottom side 290.

The functioning of the unlocking apparatus 228 is described in more detail in the following.

The receiving body 72 and the unlocking body 274 are movable in the actuating direction 318 in parallel to the ring receptacles 88 and thus in parallel to the first ring planes 58 of the ring instruments 26 for transferring the locking devices 30 of the ring instruments 26 from the locked position into the unlocked position. The actuating direction 318 thus runs in an actuating plane 354 that extends in parallel to the first and second ring planes 58 and 60.

The receiving body 72 and the unlocking body 274 are displaceable relative to one another in the actuating plane 354. Such a displacement movement is guided by means of the linear movement guidance device 340. The actuating direction 318 runs transversely, namely perpendicularly, to the longitudinal direction 80 of the receiving body 72.

Upon a movement of the unlocking body 274 in the actuating direction 318 toward the receiving body 72, the second rings 56 each abut against one of the unlocking faces 316 of the unlocking body 274 and slide on the unlocking faces 316 with progressive movement of the unlocking body 274 toward the receiving body 72. Upon sliding, the second rings 56 are moved out of the first ring plane 58 in the direction toward the first end face 100. As a result of this sideways movement of the second rings 56, the locking elements 62 and 64 of the locking device 30 interengaging in the locked position are brought out of engagement.

Schematically depicted in FIGS. 15, 16, and 17 is the unlocking apparatus 228 with ten ring instruments 26 accommodated therein, which assume the locked position.

Schematically depicted in FIGS. 18, 19, and 21 is how the locking devices 30 are unlocked by bringing the locking elements 62 and 64 out of engagement.

When the unlocking body 274 is moved further in the direction toward the receiving body 72, the second rings 56 slide out of the ring receptacles 288 on the unlocking body top side 278. The second rings 56 thereby spring back into their basic position in which the first ring plane 58 and the second ring plane 60 of each ring instrument 26 coincide. Now, for example, a rod-shaped holding member 328 can be guided through the second rings 56. This is shown schematically in FIG. 22.

When the unlocking body 274 is moved out of the proximate position depicted in FIG. 20 back into the starting position in which the unlocking body 274 is spaced at a maximum distance from the receiving body 72, the ring instruments 26 can be opened. The movement for opening takes place in an opening direction symbolized by the arrow 330 in FIG. 22. When opening the ring instruments 26, the rings 54 and 56 are pivoted relative to one another about the pivot axis 44. In this open position depicted in FIG. 22, the unlocking apparatus 228 can serve to store the ring instruments 26 in the sieve basket 10, namely both during washing and during hot steam sterilization of the ring instruments 26.

Schematically depicted in FIGS. 23 to 25 is a further embodiment of an unlocking apparatus denoted as a whole with the reference numeral 428.

The unlocking apparatus 428 differs from the unlocking apparatus 228 in that it comprises a pivotal movement guidance device 540 instead of the linear movement guidance device 340. The pivotal movement guidance device 540 comprises a pivot bearing 556, which is configured in the form of a hinge, the bands 558 and 560 of which are arranged on the receiving body 72 on the one hand and on the unlocking body 274 on the other hand. The bands 560 are fixed to the longitudinal side 285 of the unlocking body 274, the bands 558 to a longitudinal side 85 of the receiving body 72 facing oppositely away from the longitudinal side 84. A pivot axis 562 defined by the pivot bearing 556 thus runs in parallel to the longitudinal sides 85 and 285.

In the case of the unlocking apparatus 428, an actuating direction 518 runs in an actuating plane that runs perpendicularly to the pivot axis 562, i.e., extends in parallel to the ring planes 58 and 60.

The functioning of the unlocking apparatus 428 corresponds substantially to the functional principle of the unlocking apparatus 228. The difference in the two unlocking apparatuses 228 and 428 is, in particular, that in the case of the unlocking apparatus 428 the unlocking body 274 is pivoted about the pivot axis 562 toward the receiving body 72, and in the case of the unlocking apparatus 228 the unlocking body 274 is displaced in the direction toward the receiving body 72. In both cases, the second rings 56 slide on the unlocking faces 316 upon the movement of the unlocking body 274 relative to the receiving body 72, the second rings 56 thereby being laterally deflected in parallel to the longitudinal direction 80, such that the locking elements 62 and 64 of the locking devices 30 can come out of engagement.

In the case of the unlocking apparatus 428, an actuating lever may optionally be provided, which can be fixed to the unlocking body 274. For example, said actuating lever may be configured in the form of an eccentric lever in order to make it possible for a user to pivot the unlocking body 274 about the pivot axis 562 toward the receiving body 72 with as little effort as possible in order to simultaneously unlock all ten ring instruments 26 accommodated in the unlocking apparatus 428.

Schematically depicted in FIG. 26 and denoted as a whole with the reference numeral 628 is a further embodiment of an unlocking apparatus. The unlocking apparatus 628 comprises a receiving body 672 and an unlocking body 674.

The receiving body 672 is similar in its structure to the receiving body 72. However, a width of the ring receptacles 688 increases commencing from the ring receptacle located nearest the second end face 702 to the ring receptacle 688 located nearest the first end face 700. This is necessary due to the particular design of the unlocking elements 712.

The ring receptacles 788 of the unlocking body 674 differ from one another due to a differing inclination of the unlocking faces 716. The unlocking planes 722 defined by the unlocking faces 716 each enclose with the abutment planes 720 defined by the abutment surfaces 714 an angle of inclination 750 that successively increases commencing from the unlocking element 712 located nearest the second end face 702 to the unlocking element 712 located nearest the first end face 700.

The unlocking body 674 may selectively be moved linearly relative to the receiving body 672 or, like in the case of the unlocking apparatus 428, be pivoted.

The unlocking faces 716 form sliding surfaces for the second rings 56, which are not depicted in FIG. 26 for the sake of clarity. Due to the different angles of inclination 750, not all locking devices 30 of the ring instruments 26 accommodated in the ring receptacles 688 and 788 are unlocked simultaneously, but rather one after the other, i.e. successively. The ring instrument 26 whose second ring 56 abuts against the unlocking face 716 located nearest the first end face 700 is unlocked first. The angle of inclination 750 is greatest here, such that even when the unlocking body 674 on only slightly advanced toward receiving body 672, the second ring 56 is deflected laterally so far that the locking elements 62 and 64 of the locking device 30 of this ring instruments 26 come out of engagement, the other ring instruments 26 that are accommodated in the unlocking apparatus 628 still assuming the locked position.

In the case of the unlocking device 628, the angles of inclination 780 of adjacent unlocking faces 716 increase successively. An angle of change, i.e., the angle by which the angles of inclination 750 of adjacent unlocking faces 716 differ, is in a range of about 1° to about 10°.

A further embodiment of an unlocking apparatus denoted as a whole with the reference numeral 828 is schematically depicted in FIG. 27.

The unlocking apparatus 828 comprises a receiving body 72, as has already been described in detail above.

The unlocking body 874 is similar to the unlocking body 274. The unlocking elements 912 comprise unlocking faces 916, which define unlocking planes 922 that enclose an angle of inclination 950 with the abutment planes 120. The angle of inclination 950 is identical for all unlocking elements 912.

However, the unlocking elements 912 differ from the unlocking elements 312 in that a distance 970 of ends 952 of the unlocking faces 916 pointing in the direction toward the receiving body 72 from the unlocking body bottom side 890, which points in the direction toward the receiving body 72, is different. In the embodiment depicted in FIG. 27, the distance 970 increases successively from unlocking element 912 to unlocking element 912 commencing from the unlocking element 912 located nearest the second end face 102, namely up to unlocking element 912 located nearest the first end face 100.

To unlock a plurality of ring instruments 26, the first rings 54 are inserted into the ring receptacles 88 of the receiving body 72. When the unlocking body 874 is displaced or pivoted in the actuating direction 918 in the direction toward the receiving body 72, the second rings 56 of the ring instruments 26 successively come into contact with the unlocking faces 916, namely first the second ring 56 of the ring instrument 26 arranged nearest the second end face 102 with the unlocking face 916 of the unlocking element 912 located nearest the second end face 102. The ring instruments 26 are thus successively unlocked with the unlocking apparatus 828, similar to the unlocking apparatus 628, although a different principle is used in the case of the unlocking apparatus 828 than in the case of the unlocking apparatus 628.

Not depicted in the Figures is a coupling device that is optionally arranged or formed on the receiving bodies 72 and 672 for coupling to the sieve basket 10 in a force-locking and/or positive-locking manner in a coupling position. The coupling device may comprise, in particular, coupling elements that are in force-locking and/or positive-locking engagement with the perforations 24 of the sieve basket 10 in the coupling position. For example, the coupling device may comprise coupling projections made of a plastic that is elastic and is clampingly held in a perforation 24 on the sieve basket 10 in the coupling position. The coupling device may further also comprise hooks that engage in the perforations 24.

The unlocking apparatuses 28, 228, 428, 628, and 828 described above are made of materials that are sterilizable with hot steam. The described receiving and unlocking bodies are made of a plastic. Said plastic may be polyetheretherketone (PEEK) in certain embodiments. The grip elements and the guidance elements of the linear movement guidance device and the pivotal movement guidance device may be made of a metallic material, for example an instrument steel.

With the described unlocking apparatuses 28, 228, 428, 628 and 828, two or more ring instruments 26 can be simultaneously or successively unlocked in a simple manner and in a manner that is effortless for a user and, as necessary, can be stored in a sieve basket, in particular for reprocessing the ring instruments 26 in a washing machine or a hot steam sterilization device.

The invention claimed is:

1. An unlocking apparatus for unlocking locking devices of at least two medical ring instruments, said locking devices comprising cooperating locking elements, wherein the cooperating locking elements are in at least one of force-locking and positive-locking engagement in a locked position and are out of engagement in an unlocked position, wherein the at least two medical ring instruments each comprise a first branch with a first distal end and a first proximal end and each comprise a second branch with a second distal end and a second proximal end, wherein the first branch and the second branch of each ring instrument are mounted on one another so as to be pivotable about a pivot axis, wherein a first ring is arranged or formed on the first proximal end of the first branch of each ring instrument and wherein a second ring is arranged or formed on the second proximal end of the second branch of each ring instrument, wherein each first ring defines a first ring plane and wherein each second ring defines a second ring plane, wherein the first ring plane and the second ring plane of each ring instrument run in parallel or substantially in parallel to one another, wherein the pivot axis runs transversely to at least one of the first ring plane and the second ring plane, wherein the unlocking apparatus comprises a receiving body with at least two ring receptacles for accommodating the first rings of the at least two medical ring instruments, wherein the unlocking apparatus comprises an unlocking body with at least two unlocking elements cooperating with the second rings of the at least two medical ring instruments, wherein the unlocking body and the receiving body are arranged so as to be movable relative to one another in an actuating direction in such a way that the at least two unlocking elements thereby engage on the second rings and move the second rings relative to the first rings in an unlocking direction transversely to the first ring plane and to the second ring plane for transferring the locking devices of the at least two medical ring instruments from the locked position into the unlocked position.

2. The unlocking apparatus in accordance with claim 1, wherein the receiving body and the unlocking body are coupled for guiding a movement relative to one another.

3. The unlocking apparatus in accordance with claim 1, wherein the unlocking apparatus comprises at least one of a linear movement guidance device and a pivotal movement guidance device.

4. The unlocking apparatus in accordance with claim 1, wherein the receiving body comprises a plurality of ring receptacles, wherein a first ring of a ring instrument is insertable at least partially in each of the plurality of ring receptacles, and wherein the unlocking body comprises a plurality of unlocking elements.

5. The unlocking apparatus in accordance with claim 1, wherein:
   a) a number of ring receptacles of the receiving body corresponds to a number of unlocking elements of the unlocking body; and/or
   b) at least one of the at least two ring receptacles of the receiving body and the at least two unlocking elements are consecutively numbered; and/or
   c) each of the at least two ring receptacles is configured in the form of a receiving slot or a receiving groove.

6. The unlocking apparatus in accordance with claim 1, wherein each of the at least two ring receptacles has an abutment surface for an accommodated first ring and wherein the abutment surface runs in parallel or substantially in parallel to the first ring plane.

7. The unlocking apparatus in accordance with claim 1, wherein the at least two unlocking elements each have an unlocking face on which the second rings abut and/or slide upon a movement of the unlocking body and the receiving body relative to one another in the actuating direction.

8. The unlocking apparatus in accordance with claim 1, wherein the receiving body has a longitudinal perforation and wherein the longitudinal perforation passes through the at least two ring receptacles.

9. The unlocking apparatus in accordance with claim 8, wherein at least one of:
   a) the longitudinal perforation is configured as a bore; and
   b) the unlocking apparatus comprises a holding member, which is accommodated in the longitudinal perforation in a holding position.

10. The unlocking apparatus in accordance with claim 1, wherein the receiving body is of cuboidal or substantially cuboidal configuration and defines a longitudinal direction and wherein the longitudinal direction runs transversely to the ring receptacles.

11. The unlocking apparatus in accordance with claim 1, wherein the receiving body and the unlocking body are movable in a direction transverse to the at least two ring receptacles for transferring the locking devices of the at least two medical ring instruments from the locked position into the unlocked position.

12. The unlocking apparatus in accordance with claim 1, wherein the receiving body and the unlocking body are of identical configuration.

13. The unlocking apparatus in accordance with claim 1, wherein at least one of:
   a) the ring receptacles extend from a receiving body top side to a receiving body bottom side; and
   b) the receiving body and the unlocking body are movable in an opening direction for opening the at least two medical ring instruments after transferring from the locked position into the unlocked position by pivoting the first and second rings away from one another, said opening direction running transversely to the actuating direction.

14. The unlocking apparatus in accordance with claim 1, wherein the receiving body and the unlocking body are movable in the actuating direction in parallel or substantially in parallel to the at least two ring receptacles for transferring the locking devices of the at least two medical ring instruments from the locked position into the unlocked position.

15. The unlocking apparatus in accordance with claim 14, wherein at least one of:
   a) the actuating direction runs in an actuating plane that extends in parallel to at least one of the first ring planes and the second ring planes;
   b) the actuating device runs transversely to the longitudinal direction of the receiving body; and
   c) the second rings each abut against and slide on an unlocking face of the unlocking body upon a movement of the unlocking body and the receiving body relative to one another in the actuating direction.

16. The unlocking apparatus in accordance with claim 14, wherein unlocking planes defined by the unlocking faces are inclined by an angle of inclination relative to associated abutment planes.

17. The unlocking apparatus in accordance with claim 14, wherein:
   a) a distance of ends of the unlocking faces pointing in a direction toward the receiving body from an unlocking body bottom side, which points in the direction toward the receiving body, is identical; or
   b) a distance of ends of the unlocking faces pointing in the direction toward the receiving body from an unlocking body bottom side, which points in the direction toward the receiving body, is different, wherein a distance of adjacent unlocking faces from the unlocking body bottom side successively increases.

18. The unlocking apparatus in accordance with claim 1, wherein the unlocking apparatus is configured:
   a) to simultaneously release all locking devices of the at least two medical ring instruments accommodated in the unlocking apparatus upon a movement of the unlocking body and the receiving body relative to one another in the actuating direction;
   or
   b) to successively release all locking devices of the at least two medical ring instruments accommodated in the unlocking apparatus upon a movement of the unlocking body and the receiving body relative to one another in the actuating direction.

19. A sieve basket with a receiving space for accommodating surgical instruments, wherein an unlocking apparatus for unlocking locking devices of at least two medical ring instruments is arranged in the receiving space, said locking devices comprising cooperating locking elements, wherein the cooperating locking elements are in at least one of force-locking and positive-locking engagement in a locked position and are out of engagement in an unlocked position, wherein the at least two medical ring instruments each comprise a first branch with a first distal end and a first proximal end and each comprise a second branch with a second distal end and a second proximal end, wherein the first branch and the second branch of each ring instrument are mounted on one another so as to be pivotable about a pivot axis, wherein a first ring is arranged or formed on the first proximal end of the first branch of each ring instrument and wherein a second ring is arranged or formed on the second proximal end of the second branch of each ring instrument, wherein each first ring defines a first ring plane and wherein each second ring defines a second ring plane, wherein the first ring plane and the second ring plane of each ring instrument run in parallel or substantially in parallel to one another, wherein the pivot axis runs transversely to at least one of the first ring plane and the second ring plane, wherein the unlocking apparatus comprises a receiving body with at least two ring receptacles for accommodating the first rings of the at least two medical ring instruments, wherein the unlocking apparatus comprises an unlocking body with at least two unlocking elements cooperating with the second rings of the at least two medical ring instruments, wherein the unlocking body and the receiving body are arranged so as to be movable relative to one another in an actuating direction in such a way that the at least two unlocking elements thereby engage on the second rings and move the second rings relative to the first rings in an unlocking direction transversely to the first ring plane and to the second ring plane for transferring the locking devices of the at least two medical ring instruments from the locked position into the unlocked position.

20. The sieve basket in accordance with claim 19, wherein the sieve basket comprises a sieve basket base and sieve basket walls extending transversely away from the sieve basket base, wherein the sieve basket base and the sieve basket walls delimit the receiving space, and wherein at least one of the sieve basket base and the sieve basket walls are provided with a plurality of perforations.

\* \* \* \* \*